US010808239B2

(12) United States Patent
Drewlo et al.

(10) Patent No.: US 10,808,239 B2
(45) Date of Patent: Oct. 20, 2020

(54) ISOLATION AND ANALYSIS OF FETAL DNA FROM EXTRAVILLOUS TROPHOBLAST CELLS RETRIEVED FROM THE ENDOCERVICAL CANAL

(71) Applicant: Wayne State University, Detroit, MI (US)

(72) Inventors: Sascha Drewlo, Grand Rapids, MI (US); D. Randall Armant, Saint Clair Shores, MI (US)

(73) Assignee: Wayne State University, Detroit, MI (US)

( * ) Notice: Subject to any disclaimer, the term of this patent is extended or adjusted under 35 U.S.C. 154(b) by 93 days.

(21) Appl. No.: 16/091,413

(22) PCT Filed: Apr. 6, 2017

(86) PCT No.: PCT/US2017/026335
§ 371 (c)(1),
(2) Date: Oct. 4, 2018

(87) PCT Pub. No.: WO2017/176985
PCT Pub. Date: Oct. 12, 2017

(65) Prior Publication Data
US 2019/0153431 A1 May 23, 2019

Related U.S. Application Data

(60) Provisional application No. 62/318,982, filed on Apr. 6, 2016.

(51) Int. Cl.
*C12N 15/10* (2006.01)
*C12Q 1/6806* (2018.01)
*G01N 33/50* (2006.01)

(52) U.S. Cl.
CPC ....... *C12N 15/1003* (2013.01); *C12Q 1/6806* (2013.01); *G01N 33/50* (2013.01)

(58) Field of Classification Search
None
See application file for complete search history.

(56) References Cited

U.S. PATENT DOCUMENTS

| | | | |
|---|---|---|---|
| 5,447,864 | A | 9/1995 | Raybuck et al. |
| 5,858,649 | A | 1/1999 | Asgari et al. |
| 2002/0009759 | A1 | 1/2002 | Terstappen et al. |
| 2004/0197832 | A1 | 10/2004 | Amiel et al. |
| 2005/0123914 | A1 | 6/2005 | Katz et al. |
| 2005/0181429 | A1 | 8/2005 | Fejgin et al. |
| 2007/0224597 | A1 | 9/2007 | Pircher et al. |
| 2008/0261822 | A1 | 10/2008 | Fejgin et al. |
| 2009/0286271 | A1 | 11/2009 | Karumanchi et al. |
| 2011/0027795 | A1 | 2/2011 | Mantzaris et al. |
| 2011/0183338 | A1 | 7/2011 | Bischoff |
| 2012/0149014 | A1 | 6/2012 | Allman et al. |
| 2013/0171672 | A1 | 7/2013 | Hussa et al. |
| 2015/0267240 | A1 | 9/2015 | Armant et al. |

FOREIGN PATENT DOCUMENTS

| | | |
|---|---|---|
| WO | WO-2007/112281 A2 | 10/2007 |
| WO | WO-2010/121294 A1 | 10/2010 |
| WO | WO-2014/062995 | 4/2014 |

OTHER PUBLICATIONS

Jain, Chandni V., "Molecular Regulation of Trophoblast Survival during Placentation and Pathologies of Placental Insufficiency" (dated Jan. 1, 2016). Wayne State University Dissertations. 1642.*
Bajpayee, S., Prenatal Genetic Diagnosis Using Transcervically Derived and Immunomagnetically Isolated Trophoblast Cells, Wayne State University Honors College Theses, Dec. 13, 2012.
Bolnick, J. et al., Trophoblast retrieval and isolation from the cervix (TRIC) for noninvasive prenatal screening at 5 to 20 weeks of gestation, *Fertility and Sterility*, 102(1): 135-142, Jul. 2014.
Bolnick, A. et al., Trophoblast Retrieval and Isolation from the Cervix for Noninvasive, First Trimester, Fetal Gender Determination in a Carrier of Congenital Adrenal Hyperplasia, *Reproductive Sciences*, pp. 1-6, Feb. 25, 2016.
Bolnick, et al., Fertility and Sterility. Published online Sep. 2012, 98(3): p. S133, Abstract P-72.
Evers, D. et al., The effect of formaldehyde fixation on RNA: optimization of formaldehyde adduct removal, *The Journal of Molecular Diagnostics*, 13(3): 282-288, May 1, 2011.
Fritz, R. et al., Noninvasive detection of trophoblast protein signatures linked to early pregnancy loss using trophoblast retrieval and isolation from the cervix (TRIC), *Fertility and Sterility*, 104(2): 339, Aug. 2015.
Fritz, R. et al., Trophoblast retrieval and isolation from the cervix (TRIC) is unaffected by early gestational age or maternal obesity, *Prenatal Diagnosis*, 35: 1218-22, 2015.

(Continued)

*Primary Examiner* — Carla J Myers
(74) *Attorney, Agent, or Firm* — Julie K. Staple; Dinsmore & Shohl LLP

(57) ABSTRACT

Methods of isolating DNA of a fetus of an ongoing pregnancy are provided according to the present invention which include obtaining a maternal endocervical sample containing maternal cells and fetal extravillous trophoblast cells from a pregnant subject; isolating fetal extravillous trophoblast cells from the maternal endocervical sample, producing isolated fetal extravillous trophoblast cells contaminated with maternal DNA; lysing the isolated fetal extravillous trophoblast cells; isolating fetal nuclei from the lysed fetal extravillous trophoblast cells, producing isolated fetal nuclei, thereby removing at least a portion of the contaminating maternal DNA; and purifying genomic DNA from the isolated fetal nuclei, producing purified fetal genomic DNA. The purified fetal genomic DNA can be assayed to determine a characteristic of a genomic DNA sequence of the purified fetal genomic DNA, thereby determining a characteristic of DNA of a fetus of an ongoing pregnancy.

19 Claims, 9 Drawing Sheets

(56) References Cited

OTHER PUBLICATIONS

Grutzkau et al., Small But Mighty: How the MACS®—Technology Based on Nanosized Superparamagnetic Particles has Helped to Analyze the Immune System Within the Last 20 Years, *Cytometry*, 77A: 643-647, May 2010.

Huang, Y. et al., Acquisition of fetal cells from transcervical cells in early pregnancy and immunocytochemical study, Dept. of Obstetrics and Gynecology, Nanfang Hospital, Southern Medical University, Guangahou, China (Abstract).

Imudia, A. et al., Transcervical Retrieval of Fetal Cells in the Practice of Modern Medicine: A Review of the Current Literature and Future Direction, *Fertil Steril*, 93(6): 1725-30, Apr. 2010.

Imudia, A. et al., Retrieval of trophoblast cells from the cervical canal for prediction of abnormal pregnancy: a pilot study, *Human Reproduction*, 24(9): 2086-92, Jun. 4, 2009.

Katz-Jaffe, M. et al., DNA identification of fetal cells isolated from cervical mucus: potential for early non-invasive prenatal diagnosis, BJOG: An International Journal of Obstetrics and Gynecology, 112: 595-600, May 2005.

Pfeifer, I. et al., Cervical trophoblasts for non-invasive single-cell genotyping and prenatal diagnosis, *Placenta*, 37: 56-60, 2016.

Wong, H., Isolation of human leukocyte antigen G/cytokeratin 7 positive fetal cells from transcervical samples for potential use in prenatal genetic diagnosis, A thesis submitted in partial fulfillment of the requirements for the Degree of Master of Philosophy at The University of Hong Kong, Jan. 2015.

\* cited by examiner

ISOLATION AND ANALYSIS OF FETAL DNA FROM EXTRAVILLOUS TROPHOBLAST CELLS RETRIEVED FROM THE ENDOCERVICAL CANAL

REFERENCE TO RELATED APPLICATION

This application claims priority to U.S. Provisional Patent Application Ser. No. 62/318,982, filed Apr. 6, 2016, the entire content of which is incorporated herein by reference.

FIELD OF THE INVENTION

Generally, the present disclosure relates to methods for analyzing fetal DNA. According to specific aspects, the disclosure relates to methods of isolating DNA from fetal extravillous trophoblast cells from a pregnant subject and analyzing the fetal DNA.

BACKGROUND OF THE INVENTION

Analysis of the fetal genome is useful for the detection of various genetic disorders to determine risk for the fetus. Currently, perinatal diagnosis is performed invasively using amniocentesis, chorion-villous sampling and blood-derived cell-free DNA with various degrees of risk and precision.

"Cell-free" methodologies of analyzing fetal DNA are limited by degradation of the fetal DNA, such that the majority of fetal DNA in blood samples are about 143 bp (Wong et al., Annu Rev. Med, 67:419-432, 2016.) Further, the "fetal fraction" of DNA isolated by "cell-free" methodologies from blood samples is limited to 10-20%. The term "fetal fraction" refers to the fraction of DNA in a sample which is fetal DNA, wherein the remainder is maternal DNA. The fetal fraction relates conversely to the term "maternal contamination." Thus, for example, where the fetal fraction of DNA in a sample is 10%, the sample is characterized by 90% maternal contamination.

Endocervical samples obtained during an ongoing pregnancy are unique among fetal cell-containing samples. Extravillous trophoblast cells of fetal origin are naturally shed into the lower uterine pole. While it would seem that an endocervical sample containing these fetal extravillous trophoblast cells would be a useful source of fetal genomic DNA for analysis of the fetal genome, it has not been possible to reliably analyze fetal genomic DNA obtained by traditional DNA extraction from fetal extravillous trophoblasts. Surprisingly, sequencing of fetal DNA isolated from highly-purified fetal extravillous trophoblast cells fails to produce a reliable fetal DNA signal.

Endocervical samples obtained during an ongoing pregnancy contain many more maternal cells than fetal trophoblast cells. Unexpectedly, it has been found by the present inventors that even after isolation of extravillous fetal trophoblast cells so that few or no maternal cells are present, significant amounts of maternal genomic DNA are associated with the fetal extravillous trophoblast cells. Without wishing to be bound by theoretical considerations, the inventors consider it possible that maternal DNA is released by senescent maternal cells in the endocervical samples and that this maternal DNA, likely degraded, is associated with the plasma membranes of fetal extravillous trophoblast cells in the endocervical samples. This previously unknown problem has caused significant issues with fetal genomic analysis using fetal extravillous trophoblast cells of endocervical samples as a source of fetal genomic DNA. Thus, there is a continuing need for more accurate genomic fetal DNA assays.

SUMMARY OF THE INVENTION

Methods of isolating DNA of a fetus of an ongoing pregnancy are provided according to the present invention which include: obtaining a maternal endocervical sample containing maternal cells and fetal extravillous trophoblast cells from a pregnant subject; isolating fetal extravillous trophoblast cells from the maternal endocervical sample, producing isolated fetal extravillous trophoblast cells contaminated with maternal DNA; lysing the isolated fetal extravillous trophoblast cells; isolating fetal nuclei from the lysed fetal extravillous trophoblast cells, producing isolated fetal nuclei, thereby removing at least a portion of the contaminating maternal DNA; lysing the isolated fetal nuclei; and purifying genomic DNA from the isolated fetal nuclei, producing purified fetal genomic DNA.

Methods of isolating DNA of a fetus of an ongoing pregnancy are provided according to the present invention which include: obtaining a maternal endocervical sample containing maternal cells and fetal extravillous trophoblast cells from a pregnant subject; isolating fetal extravillous trophoblast cells from the maternal endocervical sample, producing isolated fetal extravillous trophoblast cells contaminated with maternal DNA; lysing the isolated fetal extravillous trophoblast cells; isolating fetal nuclei from the lysed fetal extravillous trophoblast cells, producing isolated fetal nuclei, thereby removing at least a portion of the contaminating maternal DNA; further treating the isolated fetal nuclei to remove at least a further portion of the contaminating maternal DNA; lysing the isolated fetal nuclei; and purifying genomic DNA from the isolated fetal nuclei, producing purified fetal genomic DNA.

Methods of isolating DNA of a fetus of an ongoing pregnancy are provided according to the present invention which include: obtaining a maternal endocervical sample containing maternal cells and fetal extravillous trophoblast cells from a pregnant subject; isolating fetal extravillous trophoblast cells from the maternal endocervical sample, producing isolated fetal extravillous trophoblast cells contaminated with maternal DNA; lysing the isolated fetal extravillous trophoblast cells; isolating fetal nuclei from the lysed fetal extravillous trophoblast cells, producing isolated fetal nuclei, thereby removing at least a portion of the contaminating maternal DNA; further treating the isolated fetal nuclei to remove at least a further portion of the contaminating maternal DNA; lysing the isolated fetal nuclei; and purifying genomic DNA from the isolated fetal nuclei, producing purified fetal genomic DNA.

Optionally, the isolated fetal nuclei are treated with a DNAse prior to lysing the isolated fetal nuclei, thereby removing at least a portion of the contaminating maternal DNA.

Optionally, the isolated extravillous trophoblast cells are treated with a DNAse prior to isolating fetal extravillous trophoblast cells from the maternal endocervical sample, thereby removing at least a portion of the contaminating maternal DNA.

In a further option, the isolated extravillous trophoblast cells are treated with a DNAse prior to lysing isolated fetal extravillous trophoblast cells, thereby removing at least a portion of the contaminating maternal DNA.

In a still further option, the fetal extravillous trophoblast cells are fixed prior to treating the fetal extravillous trophoblast cells with the DNAse and the DNAse is attached to a support, preventing entry of the DNAse into the fetal extravillous trophoblast cells.

Optionally, the fetal extravillous trophoblast cells are not fixed prior to treating the fetal extravillous trophoblast cells with the DNAse.

According to aspects of methods of isolating DNA of a fetus of an ongoing pregnancy of the present invention, the purified fetal genomic DNA is characterized by a fetal fraction in the range of 10%-100%.

According to aspects of methods of isolating DNA of a fetus of an ongoing pregnancy of the present invention, the purified fetal genomic DNA is characterized by a fetal fraction in the range of 25%-100%.

Methods of assaying DNA of a fetus of an ongoing pregnancy are provided according to the present invention which include: obtaining a maternal endocervical sample containing fetal extravillous trophoblast cells from a pregnant subject; isolating fetal extravillous trophoblast cells from the maternal endocervical sample; lysing the isolated fetal extravillous trophoblast cells; isolating fetal nuclei from the lysed fetal extravillous trophoblast cells; lysing the isolated fetal nuclei and purifying genomic DNA from the isolated fetal nuclei; and assaying the purified fetal genomic DNA, thereby determining a characteristic of a genomic DNA sequence of the purified fetal genomic DNA, and thereby assaying genomic DNA of a fetus of an ongoing pregnancy.

Optionally, assaying the purified fetal genomic DNA according to aspects of the present invention determines a characteristic of at least one individual nucleotide in a genomic DNA sequence of the purified fetal genomic DNA, thereby assaying DNA of a fetus of an ongoing pregnancy with single base resolution.

Optionally, assaying the purified fetal genomic DNA according to aspects of the present invention includes performing a method selected from the group consisting of: sequencing, high resolution melt analysis, methylation analysis, capillary electrophoresis, mass spectrometry, single strand conformation polymorphism, single base extension, restriction fragment length polymorphism using the purified fetal genomic DNA.

Optionally, sequencing the purified fetal genomic DNA according to aspects of the present invention includes performing a method selected from the group consisting of: massively parallel signature sequencing, single-molecule real-time sequencing, polony sequencing, ion semiconductor, pyrosequencing, sequencing by synthesis, sequencing by ligation and chain termination sequencing.

According to aspects of the present invention, methods of assaying DNA of a fetus of an ongoing pregnancy are provided according to the present invention which include: obtaining a maternal endocervical sample containing fetal extravillous trophoblast cells from a pregnant subject; isolating fetal extravillous trophoblast cells from the maternal endocervical sample; treating the isolated fetal nuclei to remove at least a portion of the contaminating maternal DNA; lysing the isolated fetal extravillous trophoblast cells; isolating fetal nuclei from the lysed fetal extravillous trophoblast cells; lysing the isolated fetal nuclei and purifying genomic DNA from the isolated fetal nuclei; and assaying the purified fetal genomic DNA, thereby determining a characteristic of a genomic DNA sequence of the purified fetal genomic DNA, and thereby assaying genomic DNA of a fetus of an ongoing pregnancy.

Optionally, methods of assaying DNA of a fetus of an ongoing pregnancy provided according to the present invention include treating the isolated extravillous trophoblast cells with a DNAse prior to isolating fetal extravillous trophoblast cells from the maternal endocervical sample, thereby removing at least a portion of the contaminating maternal DNA.

Optionally, methods of assaying DNA of a fetus of an ongoing pregnancy provided according to the present invention include treating the isolated extravillous trophoblast cells with a DNAse prior to lysing isolated fetal extravillous trophoblast cells, thereby removing at least a portion of the contaminating maternal DNA.

Methods of assaying DNA of a fetus of an ongoing pregnancy are provided according to the present invention which include: obtaining a maternal endocervical sample containing fetal extravillous trophoblast cells from a pregnant subject; isolating fetal extravillous trophoblast cells from the maternal endocervical sample; lysing the isolated fetal extravillous trophoblast cells; isolating fetal nuclei from the lysed fetal extravillous trophoblast cells; lysing the isolated fetal nuclei and purifying genomic DNA from the isolated fetal nuclei; and assaying the purified fetal genomic DNA, wherein the fetal extravillous trophoblast cells are fixed prior to treating the fetal extravillous trophoblast cells with the DNAse and the DNAse is attached to a support, preventing entry of the DNAse into the fetal extravillous trophoblast cells, thereby determining a characteristic of a genomic DNA sequence of the purified fetal genomic DNA, and thereby assaying genomic DNA of a fetus of an ongoing pregnancy.

Methods of assaying DNA of a fetus of an ongoing pregnancy are provided according to the present invention which include: obtaining a maternal endocervical sample containing fetal extravillous trophoblast cells from a pregnant subject; isolating fetal extravillous trophoblast cells from the maternal endocervical sample; lysing the isolated fetal extravillous trophoblast cells; isolating fetal nuclei from the lysed fetal extravillous trophoblast cells; lysing the isolated fetal nuclei and purifying genomic DNA from the isolated fetal nuclei; and assaying the purified fetal genomic DNA, wherein the fetal extravillous trophoblast cells are not fixed prior to treating the fetal extravillous trophoblast cells with the DNAse, thereby determining a characteristic of a genomic DNA sequence of the purified fetal genomic DNA, and thereby assaying genomic DNA of a fetus of an ongoing pregnancy.

According to aspects of methods of assaying DNA of a fetus of an ongoing pregnancy of the present invention, the purified fetal genomic DNA is characterized by a fetal fraction in the range of 10%-100%.

According to aspects of methods of assaying DNA of a fetus of an ongoing pregnancy of the present invention, the purified fetal genomic DNA is characterized by a fetal fraction in the range of 25%-100%.

DETAILED DESCRIPTION OF THE INVENTION

Figure 1:
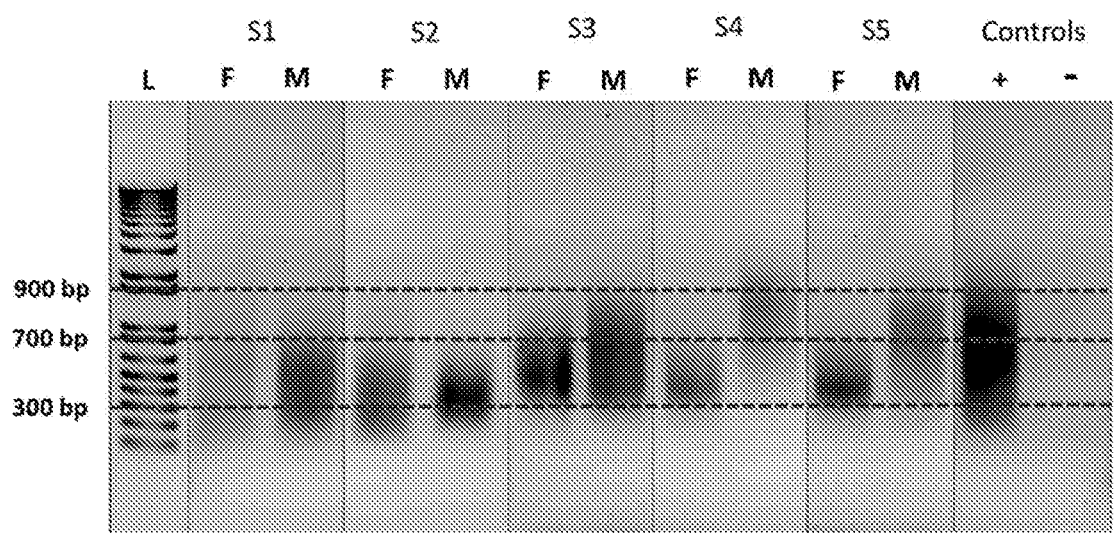
FIG. 1 is an image of a gel which shows amplified DNA of fetal and maternal cells in five independent samples, plus positive and negative controls; the amplified DNA is depicted as a smear between 700 and 900 base pair length, as shown by the DNA standard size markers (L)

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

The term "TRIC" is used herein to refer to fetal trophoblasts obtained by a TRIC "Trophoblast Retrieval and Isolation form the Cervix" method. TRIC is a method of safe non-invasive fetal cell isolation from the cervical canal in ongoing pregnancies, see description in the examples.

Methods for isolation of genomic DNA from cells of a fetus of an ongoing pregnancy and assay of the fetal genomic DNA are provided according to aspects of the present invention. Analysis of fetal cell genomic DNA provides detailed information about the fetus, such as detection of fetal abnormalities or variations, including single nucleotide polymorphisms, base modifications and detailed genomic DNA sequence information.

Methods according to aspects of the present invention include purifying genomic DNA from isolated fetal extravillous trophoblast cell nuclei, producing purified fetal genomic DNA wherein the fetal fraction is in the range of 10%-100%. Methods according to aspects of the present invention include purifying genomic DNA from isolated fetal extravillous trophoblast cell nuclei, producing purified fetal genomic DNA wherein the fetal fraction is in the range of 25%-100%. Methods according to aspects of the present invention include purifying genomic DNA from isolated fetal extravillous trophoblast cell nuclei, producing purified fetal genomic DNA wherein the fetal fraction is 50% or greater. Methods according to aspects of the present invention include purifying genomic DNA from isolated fetal extravillous trophoblast cell nuclei, producing purified fetal genomic DNA wherein the fetal fraction is 75% or greater. Methods according to aspects of the present invention include purifying genomic DNA from the isolated fetal extravillous trophoblast cell nuclei, producing purified fetal genomic DNA wherein the fetal fraction is 15%, 20%, 25%, 30%, 35%, 40%, 45%, 50%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater. As mentioned, since the fetal fraction is conversely related to contamination with maternal DNA, the purified fetal genomic DNA is characterized as having from 0%-90% maternal contamination. Methods according to aspects of the present invention include purifying genomic DNA from the isolated fetal extravillous trophoblast cell nuclei, producing purified fetal genomic DNA wherein the maternal contamination is 85%, 80%, 75%, 70%, 65%, 60%, 55%, 50%, 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less. Methods according to aspects of the present invention include purifying genomic DNA from the isolated fetal extravillous trophoblast cell nuclei, producing purified fetal genomic DNA wherein the maternal contamination is 75%, 70%, 65%, 60%, 55%, 50%, 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less.

Methods of the present invention allow for purification and assay of fetal genomic DNA in spite of the overwhelming maternal cell population in an endocervical sample. Methods of the present invention provide, for the first time, clinically relevant fetal genomic data as early as gestational age four to five weeks from ongoing pregnancies. Gestational age is well-known to be defined as the time measured from the date of onset of the last menstrual period. Methods of the present invention are not hampered by factors such as body mass index or gestational age which complicate cell-free DNA assessment methods.

While compositions and methods described herein with particular reference to human females and human fetuses, they are not limited to humans and fetal genomic DNA of other species may be similarly isolated and analyzed.

Methods according to aspects of the present invention include obtaining a maternal endocervical sample containing fetal extravillous trophoblast cells from a pregnant subject; isolating fetal extravillous trophoblast cells from the maternal endocervical sample; lysing the isolated fetal extravillous trophoblast cells; isolating fetal extravillous trophoblast cell nuclei from the lysed fetal extravillous trophoblast cells; and purifying genomic DNA from the isolated fetal extravillous trophoblast cell nuclei, thereby isolating the fetal genomic DNA from extravillous trophoblast cells.

A maternal endocervical sample is collected from a pregnant female from gestational age of about 4 weeks to about 30 weeks of pregnancy, such as in the first trimester, second trimester and/or third trimester of pregnancy.

According to aspects of the present invention, a sample is collected from a pregnant subject at about two weeks after conception (gestational age 4 weeks) up to about 20 weeks of gestation (mid-point of pregnancy) or later.

According to aspects of the present invention, isolating fetal extravillous trophoblast cells from the maternal endocervical sample is accomplished by contacting the fetal extravillous trophoblast cells with an antibody specific for the fetal extravillous trophoblast cells, wherein the antibody does not bind to maternal cells in the maternal endocervical sample, and capturing the fetal extravillous trophoblast cells attached to the antibodies.

According to particular aspects of methods of the present invention, the antibody is specific for major histocompatibility complex, class I, G (HLA-G).

Optionally, the antibody specific for the fetal extravillous trophoblast cells is attached to any solid or semi-solid support which is insoluble in aqueous solutions. Attachment of the antibody to the support is achieved by any of various methods, illustratively including adsorption to the support and chemical bonding to the support.

The antibody specific for the fetal extravillous trophoblast cells can be directly or indirectly attached to a support. The term "directly attached" is used to indicate that the support is covalently or non-covalently bound to the antibody specific for the fetal extravillous trophoblast cells and that the support is not bound to the antibody via a secondary antibody. The term "indirectly attached" is used to indicate that the antibody specific for the fetal extravillous trophoblast cells is covalently or non-covalently bound to the support via an intermediate, such as a secondary antibody or linker.

According to aspects of the present invention, the antibody specific for the fetal extravillous trophoblast cells is indirectly bound to the support via binding of the antibody to a Protein A or Protein G molecule, wherein the Protein A or Protein G molecule is bound to the support.

The insoluble solid or semi-solid support can be any of various materials such as glass; plastic, such as polypropylene, polystyrene, nylon; paper; silicon; nitrocellulose; or any other material to which a desired material can be attached without significant inhibition of the function of the material. The support can be in any of various forms or shapes, including planar, such as silicon chips and glass plates; and three-dimensional, such as particles, microtiter plates, microtiter wells, pins, fibers and the like.

In particular aspects, an insoluble solid or semi-solid support is a particle.

The particles can be of any shape, such as cylindrical, spherical, and so forth, size, composition, or physiochemical characteristics. The particle size or composition can be chosen so that the particle can be separated from fluid, e.g., on a filter with a particular pore size or by some other physical property.

The particles used can have a diameter of less than one millimeter, for example, a size ranging from about 0.1 to about 1,000 micrometers in diameter, inclusive, such as about 3-25 microns in diameter, inclusive, or about 5-10 microns in diameter, inclusive, 1 nanometer (nm) to about 100,000 nm in diameter, inclusive, for example, a size ranging from about 10-1,000 nm, inclusive, or for example, a size ranging from 200-500 nm, inclusive. In certain embodiments, particles used are beads, particularly microbeads and nanobeads.

An insoluble solid or semi-solid support can include functional groups for binding to a material to be bound to the support. For example, a support can include carboxyl, amine, amino, carboxylate, halide, ester, alcohol, carbamide, aldehyde, chloromethyl, sulfur oxide, nitrogen oxide, epoxy and/or tosyl functional groups. Functional groups, modification thereof and binding of a material, such as an antibody or enzyme, to a support are known in the art. In a particular example, 1-ethyl-3-[3-dimethylaminopropyl]carbodiimide hydrochloride, EDC or EDAC chemistry, can be used to attach a desired material to an insoluble solid or semi-solid support.

According to particular aspects of methods of the present invention, an antibody specific for the fetal extravillous trophoblast cells is directly attached to a plurality of magnetic particles and removing fetal extravillous trophoblast cells from the maternal endocervical sample includes exposure of the magnetic particles to a magnet.

Magnetic nanoparticles directly coupled to the antibody which specifically binds to a fetal antigen typically have a size in the range of 10 nm-1 um, although smaller or larger magnetic nanoparticles may be used.

According to particular aspects of methods of the present invention, HLA-G antibody is attached to magnetic nanoparticles.

Optionally, cells of the maternal endocervical sample are fixed by treatment with a fixative, wherein the treatment with the fixative is performed prior to or following isolating fetal extravillous trophoblast cells from the maternal endocervical sample.

The fixative used can be glutaraldehyde; formaldehyde; paraformaldehyde; or a combination of any two or more thereof. According to particular aspects of methods of the present invention, the aldehyde fixative is paraformaldehyde. According to further aspects of the present invention, the fixative is a non-aldehyde fixative.

Non-aldehyde fixatives illustratively include acetone, acetic acid, and alcohols such as ethanol and methanol. Combinations of two or more non-aldehyde fixatives are optionally used. According to aspects of the present invention, a mixture of methanol and acetic acid is used as a non-aldehyde fixative.

Optionally, the maternal endocervical sample is first fixed in a non-aldehyde fixative. The isolated fetal extravillous trophoblast cells are then optionally fixed with an aldehyde fixative. The non-aldehyde fixative and/or aldehyde fixative is optionally removed or partly removed by washing the maternal endocervical sample with a physiological liquid or buffer, such as saline or a buffer compatible with mammalian cells.

In a further option, the fetal extravillous trophoblast cells are treated with a protease and/or a glycosaminoglycan degrading enzyme (GAGase), wherein treating the fetal extravillous trophoblast cells with a protease and/or a GAGase is performed prior to or following removing fetal extravillous trophoblast cells from the maternal endocervical sample and prior to or following treatment of the fetal extravillous trophoblast cells with a nuclease.

Glycosaminoglycan degrading enzymes include, for example, hyaluronidase, heparinase and chondroitinase.

According to particular aspects of methods of the present invention, the maternal endocervical sample is not treated with a mucolytic agent. According to particular aspects of methods of the present invention, the maternal endocervical sample is not treated with a mucolytic agent selected from N-acetyl-L-cysteine, DTT, trypsin and trypsin/EDTA prior to isolation of the fetal extravillous trophoblasts. According to particular aspects of methods of the present invention, the maternal endocervical sample is not treated with one or more of a collagenase, a protease, a liberase blendzyme, and a mucolytic agent prior to isolation of the fetal extravillous trophoblasts.

Optionally, a maternal endocervical sample is acidified prior to isolating fetal extravillous trophoblast cells. An acidifying agent is optionally added to the sample bringing the pH of the sample to about pH 5-6. An acidifying agent can be any acid or acidic buffer, for example.

The isolated fetal extravillous trophoblast cells are further processed to isolate nuclei from the fetal extravillous trophoblast cells.

The isolated fetal extravillous trophoblast cells are lysed to break open the cells and release intact nuclei by any of various methods including, but not limited to, a physical, chemical, microfluidic or mixed modality method of breaking open the cells and releasing intact nuclei.

Physical cell lysis methods include, but are not limited to, homogenization, sonication, vortexing and beadbeating. Homogenization methods for lysis of cells and release of intact nuclei are exemplified by Dounce homogenization.

Chemical cell lysis methods for lysis of cells and release of intact nuclei include, but are not limited to, treatment with a hypotonic buffer and/or a non-ionic detergent. Non-ionic detergents used to lyse cells and release intact nuclei include, but are not limited to, nonyl phenoxypolyethoxylethanol (NP-40), typically in the range of 0.1-1%, octylphenoxypolyethoxyethanol and derivatives such as branched octylphenoxy poly(ethyleneoxy)ethanol (IGEPAL CA-630), typically in the range of 0.1-1%, and t-octylphenoxypolyethoxyethanol (Triton X-100), typically in the range of 0.1-5%. Optionally, the non-ionic detergent is present in a hypotonic buffer. An example cell lysis buffer to lyse isolated fetal extravillous trophoblast cells and release intact nuclei is 10 mM Hepes pH 7.5, 2 mM $MgCl_2$, 25 mM KCl, 0.5% NP-40 or 1% Triton X-100.

Chemical cell lysis methods include protease treatment, such as treatment with a protease including, but not limited to, protease K, pronase, trypsin and/or pepsin. The activity of a protease depends on concentration of the protease, pH, incubation time and temperature, all of which can be adjusted by the skilled artisan to achieve the desired extent of proteolysis. For controlled proteolysis to lyse cells and release intact nuclei, preferably enzymes with limited protein cleavage sites such as pepsin (Phe1Val, Gln4His, Glu13Ala, Ala14Leu, Leu15Tyr, Tyr16Leu, Gly23Phe, Phe24) or trypsin are used to gradually digest the cell membrane without affecting the nucleus such that the nuclear DNA remains intact.

Optionally, cells are subjected to homogenization in a hypotonic buffer with a non-ionic detergent to lyse the cells and release intact nuclei.

Microfluidic methods can be used to lyse cells and release intact nuclei, for example as described in U.S. Pat. No. 8,304,185; Nan et al., Lab Chip, 14:1060-1073, 2014; and Cui et al., Ann. Rev. Biomed. Engin., 17:267-286, 2015.

Cell lysate containing intact nuclei is further processed to isolate the intact nuclei. For example, separation of fetal extravillous trophoblast cell nuclei is accomplished by dissection, washing, differential centrifugation, filtration or microfluidic separation of the intact nuclei from other components present in the cell lysate.

Isolation of fetal extravillous trophoblast cell nuclei optionally includes centrifugation to pellet the nuclei and removal of the supernatant containing fetal extravillous trophoblast cell cytoplasm. The nuclei can be washed and centrifugation repeated one or more times.

Microfluidic techniques can be used to separate fetal extravillous trophoblast cell nuclei from other components present in the cell lysate, for example as described in U.S. Pat. No. 8,304,185; Nan et al., Lab Chip, 14:1060-1073, 2014; and Cui et al., Ann. Rev. Biomed. Engin., 17:267-286, 2015.

In a further example, fetal extravillous trophoblast cells are affixed to an insoluble solid or semi-solid support, the cells lysed and the cytoplasm washed away, leaving the nuclei on the support. Any support can be used, such as those mentioned herein.

A glass slide is a specific example of a support that can be used. Cells are easily attached to glass slides by centrifugation of the slide in contact with a sample containing cells.

Alternatively, a drop of liquid containing cells can be placed on a slide. The cells attach to the glass slide without further treatment.

A solid or semi-solid support is optionally treated with an adherence promoter to promote adherence of cells. Adherence promoters are exemplified by polycationic materials such as poly-L-lysine and poly-L-inosine; and/or extracellular matrix materials exemplified by collagen, fibronectin and laminin.

In a further example, an antibody specific for a nuclear protein of an intact nucleus accessible to the antibody without lysis of the nuclei is bound to the nuclei in order to separate the nuclei. The antibody can be bound to a support, such as those supports described herein, such that nuclei bound to the antibody are indirectly bound to the support and other materials can then be washed away. The antibody can be attached to a magnetic support, such as magnetic particles, allowing a nucleus bound to the antibody attached to a magnetic support to be separated from other components by exposure to a magnet. Antibodies specific for a nuclear protein of an intact nucleus accessible to the antibody without lysis of the nucleus include, but are not limited to, antibodies specific for nesprin proteins which are located on the surface of the outer nuclear membrane.

In a still further example, nuclei are isolated from the fetal extravillous trophoblast cell lysate by size exclusion methods, such as filtration, which allows retention of nuclei and removal of other lysate components based on difference in size.

The isolated fetal extravillous trophoblast cell nuclei are lysed by any of various methods including, but not limited to, a physical, chemical, microfluidic or mixed modality method of breaking open the nuclei and releasing genomic DNA.

Physical methods for lysis of nuclei include, but are not limited to, homogenization, sonication, vortexing and beadbeating. Homogenization methods for lysis of nuclei and release of genomic DNA are exemplified by Dounce homogenization.

Chemical cell lysis methods for lysis of nuclei and release of genomic DNA include, but are not limited to, treatment of cells with one or more detergents and/or chaotropic agents.

Lysis of isolated nuclei optionally includes treatment with a hypotonic, hypertonic buffer and/or an ionic detergent, such as SDS, typically in the range of 0.1-1%. Optionally, the ionic detergent is present in a hypotonic buffer. An example lysis buffer to lyse isolated nuclei is 400 mM NaCl, 10 mM Tris, 2 mM EDTA, pH 8.2, 0.66% SDS and 50 µg/ml proteinase K. Isolated nuclei may be subjected to homogenization in a hypotonic buffer with an ionic detergent to lyse the nuclei.

Chemical nuclei lysis methods include protease treatment, such as treatment with a protease including, but not limited to, protease K, pronase, trypsin and/or pepsin. The activity of a protease depends on concentration of the protease, pH, incubation time and temperature, all of which can be adjusted by the skilled artisan to achieve the desired extent of proteolysis.

In a further example, nuclei are affixed to an insoluble solid or semi-solid support, the nuclei lysed and the nuclear contents washed away, leaving the genomic DNA on the support. Any support can be used, such as those mentioned herein. A glass slide is a specific example of a support that can be used.

The fetal genomic DNA is isolated from the lysate of the nuclei by DNA isolation methods, exemplified by precipitation, centrifugation and washing; electrophoretic isolation such as gel electrophoresis; size exclusion chromatography; gradient centrifugation such as step gradient centrifugation or continuous gradient centrifugation.

The maternal endocervical samples, isolated fetal extravillous trophoblast cells and/or isolated fetal extravillous trophoblast cell nuclei are optionally treated to remove at least a portion of maternal DNA present in the sample but not contained in the maternal cells. Treatments to remove maternal DNA include, but are not limited to, treatment with a DNAse to digest the maternal DNA. The digested maternal DNA can then be washed away, thereby removing at least a portion of the maternal DNA. Optionally, the maternal DNA is contacted with a DNA absorbant material to absorb the maternal DNA. The absorbant material with absorbed maternal DNA is then removed, thereby removing at least a portion of the maternal DNA. A DNA absorbant material is exemplified by anti-DNA antibodies, optionally attached to a support.

The maternal endocervical sample including maternal cells and fetal extravillous trophoblast cells is optionally treated with a DNAse and/or protease, producing a DNAse-treated sample and/or a protease-treated sample. If the cells are fixed prior to DNAse and/or protease treatment, at least the DNAse, and optionally the protease, is attached to a support which cannot enter the fixed cells. Following treatment of the maternal endocervical sample with a DNase and/or protease, active DNase and/or protease is removed from the DNAse-treated sample and/or a protease-treated sample, such as by filtration, washing and/or heat-inactivation of the DNase and/or protease.

Prior to lysis, the isolated fetal extravillous trophoblast cells are optionally treated with a DNase and/or protease. If the cells are fixed prior to DNase and/or protease treatment, at least the DNAse, and optionally the protease, is attached to a support which cannot enter the fixed cells. Following treatment of the fetal extravillous trophoblast cells with a DNase and/or protease, active DNase and/or protease is removed from the DNAse-treated cells and/or a protease-treated cells, such as by filtration, washing and/or heat-inactivation of the DNase and/or protease.

Following lysis of the fetal extravillous trophoblast cells, intact fetal extravillous trophoblast cell nuclei released from the cells are optionally treated with a DNAse and/or protease. If the nuclei are fixed prior to DNAse and/or protease treatment, at least the DNAse, and optionally the protease, is attached to a support which cannot enter the fixed nuclei. Following treatment of the fetal extravillous trophoblast nuclei with a DNase and/or protease, active DNase and/or protease is removed from the DNAse-treated nuclei and/or a protease-treated nuclei, such as by filtration, washing and/or heat-inactivation of the DNase and/or protease.

One or more DNAse inhibitors is optionally included in a wash buffer following treatment of cells and/or nuclei with DNAse and during removal of the DNAse from contact with the cells and/or nuclei to protect the nuclei and DNA. Included DNAse inhibitors are exemplified by 2-mercaptoethanol, 2-nitro-5-thiocyanobenzoic acid, actin, alfa B2a, G2, G2a and M1 (non-competitive); $Ca^{2+}$, EGTA, EDTA, sodium dodecyl sulfate (SDS), calf spleen inhibitor protein, carbodiimide, cholesterol sulfate, iodoacetate and combinations of any two or more thereof.

A DNAse used in a method according to aspects of the present invention is optionally attached, such as by covalent linkage, to one or more supports, such as supports described herein, so that the DNAse cannot penetrate fixed cells or fixed nuclei. According to particular aspects of the present invention, a DNAse is attached to particles, such as beads, sized to prevent entry into fixed cells. Such particles typically have a particle diameter great than 10 nm.

According to particular aspects, intact fetal extravillous trophoblast cells are not treated with a DNAse before or after isolation from the maternal endocervical sample.

According to particular aspects, isolated fetal extravillous trophoblast nuclei are not treated with a DNAse before or after isolation from fetal extravillous trophoblast cells.

The fetal extravillous trophoblast cell genomic DNA is assayed to determine one or more characteristics of the fetal extravillous trophoblast cell DNA and is optionally compared to a standard. Assaying the fetal extravillous trophoblast cell genomic DNA includes any applicable genomic DNA assay.

Genomic DNA assays include, but are not limited to, sequencing, high resolution melt analysis, methylation analysis, capillary electrophoresis, mass spectrometry, single strand conformation polymorphism, single base extension and restriction fragment length polymorphism. Genomic DNA assays include assays to detect single nucleotide polymorphisms and assays of DNA base modifications with single base resolution such as detection of methylation at one or more single bases in a genomic DNA sequence.

Sequencing methodologies include massively parallel sequencing, single-molecule real-time sequencing, polony sequencing, ion semiconductor (Ion Torrent sequencing), pyrosequencing (454), sequencing by synthesis (Illumina), sequencing by ligation (SOLiD sequencing), chain termination (Sanger sequencing), for example.

Genomic DNA assays include, but are not limited to, dot blot; Southern blot; and DNase protection. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

Fetal genomic DNA is optionally amplified by an amplification method prior to performing a genomic DNA assay. Amplification methods include template directed primer extension mediated by a nucleic acid polymerase and a pair of primers which flank the target nucleic acid to be amplified, including, but not limited to, polymerase chain reaction (PCR), ligation-mediated PCR (LM-PCR), phi-29 PCR, real-time quantitative PCR (qPCR), whole genome amplification and other nucleic acid amplification methods, for instance, as described in C. W. Dieffenbach et al., PCR Primer: A Laboratory Manual, Cold Spring Harbor Laboratory Press, 2003; V. Demidov et al., DNA Amplification: Current Technologies and Applications, Taylor & Francis, 2004; and Kroneis, T. (Ed.), Whole Genome Amplification: Methods and Protocols (Methods in Molecular Biology), 2015, Humana Press ISBN-10: 1493929895.

Methods according to aspects of the present invention include determining a characteristic of at least one individual nucleotide in a genomic DNA sequence of the purified fetal genomic DNA, thereby assaying DNA of a fetus of an ongoing pregnancy.

Standards

Genomic DNA isolated from fetal cells is analyzed to identify genomic DNA variants, compared to a standard, in the fetal cells according to aspects of the present invention.

Standards suitable for genomic DNA assays are well-known in the art and the standard used can be any appropriate standard.

A standard may be a reference genome concurrently analyzed or previously determined in a sample of an individual control subject or in a population of control subjects and stored in a print or electronic medium for recall and comparison to a result of an assay.

Embodiments of inventive compositions and methods are illustrated in the following examples. These examples are provided for illustrative purposes and are not considered limitations on the scope of inventive compositions and methods.

EXAMPLES

Example 1

Sample Collection & Trophoblast Cell Isolation

Maternal and fetal cells were obtained from five cervical specimens at 5, 7, 14, 15 and 15 weeks of gestation. Maternal blood as well as fetal blood spot DNA from the same patients was used as reference material as available. Genomic DNA from five fetal/maternal pairs was isolated and exome sequencing performed.

Endocervical cells were obtained with a ThinPrep and immediately fixed during the PAP smear procedure, preserving proteins and nucleic acids. The collected sample was processed to separate the mucus and cells. The cells were then washed with phosphate buffered saline (PBS), centrifuged and resuspended in 1.5 mL PBS, combined with anti-HLA-G antibody coated magnetic nanoparticles, and incubated overnight at 4° C. with mixing. The HLA-G negative non-bound cells were collected after magnetic immobilization and three washings in PBS. The HLA-G positive bound cells are collected and stained for the EVT markers. The isolated HLA-G positive extravillous trophoblast (EVT) cells are referred to interchangeably as isolated fetal cells, isolated fetal extravillous trophoblast cells or isolated EVT herein and the HLA-G negative cervical cells as maternal cells.

Fluorescent Immune Hybridization

Isolated fetal extravillous trophoblast cells (HLA-G positive) were spun onto slides and stained for X and Y chromosome by the FISH technique. The samples that were positive for Y chromosome were selected for following experiments. The samples used are listed in Table I.

TABLE I

The sample IDs identified as males based on FISH and their gestational age

| Sample ID | Gestational Age | Gender for Fetus |
|---|---|---|
| 0624-4A (S1) | 14 weeks | Male |
| 1007-3A (S2) | 15 weeks 3 days | Male |
| 1028-3B (S3) | 15 weeks 5 days | Male |
| 0325-4A (S4) | 7 weeks | Male |
| 0318-4A (S5) | 5 weeks 2 days | Male |

DNA Extraction and Validation for Isolated EVT and Maternal Cells

For each sample, the fetal cell DNA was extracted from the slides used for FISH and the maternal cell DNA from the HLA-G negative cell fraction.

Isolated fetal extravillous trophoblasts on slides that were not previously used for FISH analysis, were treated as follows to remove cell membranes and cytoplasm potentially contaminated with maternal DNA leaving only isolated fetal extravillous trophoblast nuclei.

Isolated fetal extravillous trophoblast cells on the slides were incubated in freshly prepared protease solution (0.011 gm pepsin in 100 mL 0.01N HCl) for 11 min at 37° C. to lyse the cells while fetal nuclei remain intact. Cell debris was removed following lysis by washing in 1× Phosphate buffered saline (PBS, pH 7.5), leaving the intact fetal nuclei on the slides.

The isolated fetal nuclei were then lysed by incubation with a PCR compatible lysis buffer, 5 mM Tris\HCL, pH 8.8 including proteinase K, overnight at 42° C., followed by inactivation of the enzyme at 65° C. for 30 mins and 80° C. for 15 mins (The cell to buffer ratio was maintained at 1 µL buffer: 2 cells). This was followed by a standard TaqMan real-time PCR (qPCR) assay with the Copy No. probe (Applied Biosystems) to validate the DNA extraction procedure and SRY probe (Applied Biosystems) to confirm the male gender of the isolated EVT (fetal samples).

DNA from HLA-G negative maternal cells (10,000 cells) was extracted using a standard silica column based DNA purification protocol, commercially available as DNeasy Blood & Tissue Kit (Qiagen). DNA extracted was quantified using a fluorescent DNA intercalating dye assay, Pico Green Assay (Invitrogen).

DNA Extraction & Purification from Maternal and Fetal Blood Samples 2 ml blood collected from the patients was layered onto a 5 ml Ficol hypaque solution and centrifuged at 200 g for 10 mins. The leukocyte layer (buffy coat) was then aspirated into a fresh tube. Fetal blood was obtained as blood punches/spots. DNA was extracted from the buffy coat and blood spots as per manufacturer's protocol using the EZ1 DNA Blood 350 µl Kit (Qiagen) and the EZ1 DNA Investigator Kit (Qiagen) respectively. This was followed by DNA purification using the MiniElute PCR Purification Kit (Qiagen) following the manufacturer's protocol.

Whole Genome Amplification (WGA)

After DNA was extracted from the isolated EVT and maternal cells, a portion of the isolated DNA was subjected to a PCR-based WGA, Ampli 1™ Whole Genome Amplification Kit (Silicon Biosystems) which provides balanced and complete amplification of the entire genome of a cell, following the manufacturer's protocol. FIG. 1 shows amplified DNA of fetal and maternal cells from five independent samples, plus positive (+) and negative (−) controls. The amplified DNA is depicted as a smear between 700 and 900 base pairs in length, as shown by the DNA standard size markers (L). For visualization of whole genome amplification on the agarose gel in FIG. 1, 6 µL of whole genome amplified sample was mixed with 2 µL of loading buffer, loaded onto a 1% agarose gel and subjected to electrophoresis. L: Ladder F: Fetal sample, M: Maternal sample. Controls, −: Water control for amplification procedure, +: Human male genomic DNA. FIG. 1 shows a representative image.

This was followed by a 3× bead purification using a standard commercial solid phase reverse immobilization bead-based purification system, Agencourt Ampure XP paramagnetic beads. DNA binds, due to its charge to functional groups on the beads. Proteins have less affinity to beads and are washed away using the manufacturer's protocol.

To evaluate the quality of the WGA procedure, a PCR-based assay which amplifies selected regions, Amplifi 1™ QC kit (Silicon Biosystems), was used. The results of the quality control (QC) assay were evaluated using gel electrophoresis by comparing the obtained amplicon length (in base pairs, bp) with the expected ones, see Table II.

TABLE II

PCR expected product length

| Target | Chromosome | Amplicon Length (bp) |
|---|---|---|
| A | 12q | 91 |
| B | 5q | 108-166 |
| C | 17q | 299 |
| D | 6q | 614 |

Figure 2:
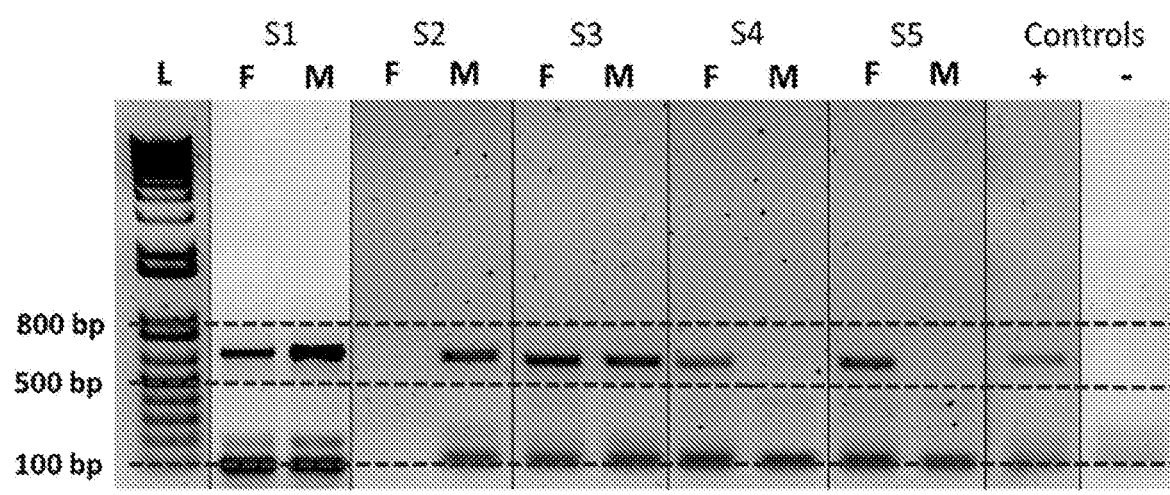
FIG. 2 is an image of a gel which shows PCR amplified fragments from various chromosomes in fetal and maternal cells from five independent samples, as well as positive and negative controls; the lengths of the fragments are between 100-800 base pairs, as indicated by the DNA standards (L)

Additionally, the WGA was visually validated by running a 6 µL aliquot of the amplified samples on 1% agarose gel. FIG. 2 shows PCR amplified fragments from various chromosomes of fetal and maternal cells from five independent samples, plus positive (+) and negative (−) controls. The lengths of the fragments are between 100-800 base pairs in length, as shown by the DNA standard size markers (L). For visualization of the QC assay for whole genome amplification on agarose gel replicates were pooled and 24 µL of the sample was mixed with 6 µL of loading buffer and loaded onto a 1% agarose gel and subjected to electrophoresis. L: Ladder F: Fetal sample, M: Maternal sample. Controls, −: Water control for amplification procedure, +: Amplified control human male genomic DNA FIG. 2 shows a representative image.

Library Preparation

DNA libraries were prepared as per manufacturer's protocol using the Nextera Rapid Capture Exome Kit (I lumina) using 50 ng of starting input of DNA. The samples and their respective fractions used for Library preparation are outlined in Table III.

TABLE III

Sample IDs and their representative fractions used for library preparation.

| SAMPLE ID | | WHOLE GENOME AMPLIFIED FRACTION | UNAMPLIFIED FRACTION |
|---|---|---|---|
| 0624-4A (S1) | Fetal | DNA isolated from FISH slides | Blood spots |
| | Maternal | HLA-G negative cervical cells | HLA-G negative cervical cells (10,000 cells) |
| 1007-3A (S2) | Fetal | DNA isolated from FISH slides | Blood spots |
| | Maternal | HLA-G negative cervical cells | Buffy coat layer |
| 1028-3B (S3) | Fetal | DNA isolated from FISH slides | Blood spots |
| | Maternal | HLA-G negative cervical cells | Buffy coat layer |
| 0325-4A (S4) | Fetal | DNA isolated from FISH slides | Blood spots |
| | Maternal | HLA-G negative cervical cells | Buffy coat layer |
| 0318-4A (S5) | Fetal | DNA isolated from FISH slides | Blood spots |
| | Maternal | HLA-G negative cervical cells | HLA-G negative cervical cells (10,000 cells) |

Figure 3:
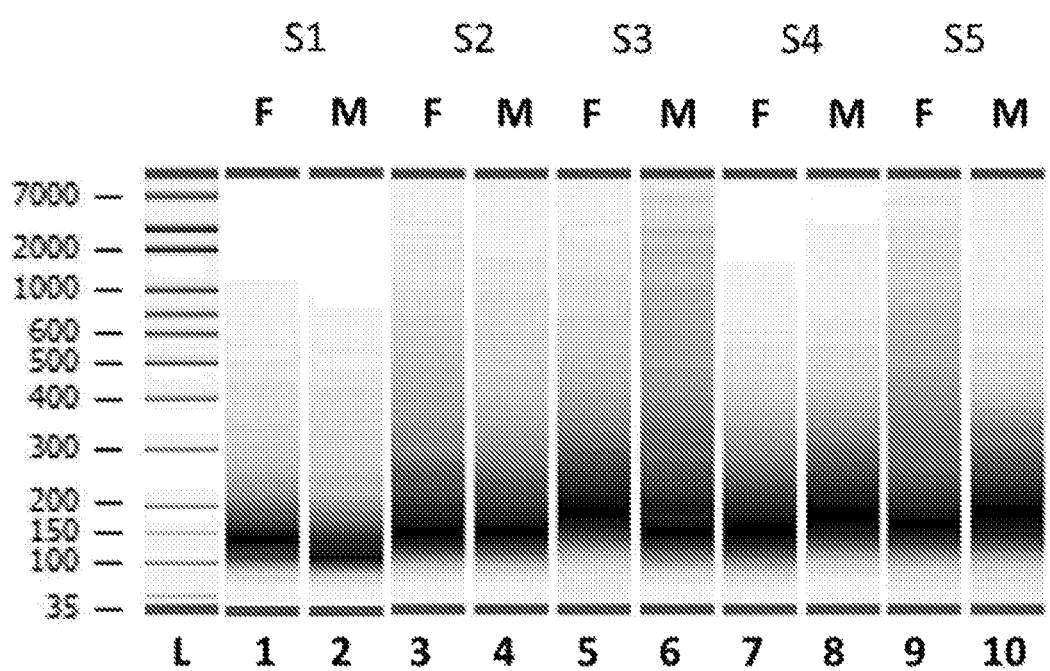
FIG. 3 is an image of a gel which shows digital electrophoretic analyses of successful library preparation from fetal (F) and maternal (M) cells in five independent samples; sizes of the DNA standard size markers (L) are indicated on the y-axis for reference.

The DNA isolated from isolated EVT and maternal cells was separately amplified in triplicate and 50 ng of the pooled replicates was used for library preparation. Whole genome amplified DNA samples and the unamplified DNA from buffy coat and blood spots was quantified using a fluorescent DNA intercalating dye assay, Pico Green Assay (Invitrogen). Uniquely barcoded adaptors were ligated to samples followed by PCR amplification and library purification. The final library pool was quantified by using a fluorescent DNA intercalating dye assay, Pico Green Assay (Invitrogen) and its quality assessed using the High Sensitivity DNA Chip (Agilent Technologies) on the bioanalyzer. FIG. 3 shows digital electrophoretic analyses of successful library preparation from fetal (F) and maternal (M) cells in five independent samples. Sizes of the DNA standard size markers (L) are indicated on the y-axis for reference.

Individual library samples were quantified by RT-PCR using a commercially available KAPA library quantification kit (KAPA Biosystems—Illumina). The DNA standards provided in the kit represent a 10-fold dilution series (20 pM to 0.0002 pM). On determination of individual concentrations, the resulting cDNAs were combined into individual libraries at a concentration of 2 nM before sequencing (multiplexed) to eliminate any sequencing lane effect.

Example 2

Method for Unstained Slides

Isolated fetal extravillous trophoblast cells (HLA-G positive) were spun onto slides. The slides are viewed under bright field microscope to outline the area with cells. The slides are immersed in freshly prepared protease solution (0.011 gm pepsin in 100 mL 0.01N HCl) for 11 min at 37° C. to lyse the cells and release intact fetal extravillous trophoblast nuclei. The slides are then washed 1× Phosphate buffered saline (PBS, pH 7.5) for 5 min at room temperature. The slides are then dehydrated by passing them through alcohol gradients ethanol 90%, 80% and 70% each for 1 min. The slides are then allowed to dry and viewed under the microscope again to ensure that there is no cell loss.

To lyse the isolated fetal extravillous trophoblast nuclei on the slides, 5-10 ul of 5 mM Tris/HCL pH 8.8/proteinase K nuclei lysis buffer (obtained commercially in an Arcturus PicoPure DNA extraction kit, Thermo Fischer), heated to 65° C. is placed in contact with the nuclei on the slide and the slide is placed on the thermocycler set at 65° C. for 1-2 min. The amount of buffer used varies and is based upon the number of cells on the slide. An additional 5 µl of nuclei lysis buffer is added and the total amount is removed from the slide and placed in a 0.2 ml tube. The final amount of nuclei lysis buffer in the tube is adjusted to maintain a ratio of 2 cells/1 µL of buffer. The slides are then visualized again to ensure all cells have been extracted. The tubes are then incubated overnight at 65° C. followed by inactivation at 95° C. for 30 mins. The success of DNA isolation is confirmed by TaqMan real-time PCR (qPCR) assay with the Copy No. probe (Applied Biosystems) and SRY probe (Applied Biosystems) to confirm the gender.

DNA Extraction and Validation for Isolated EVT and Maternal Cells

For Whole Genome Amplifications:

For each sample, the fetal extravillous trophoblast cell DNA was extracted from isolated nuclei on slides following cell lysis. Maternal cell DNA was isolated from the HLA-G negative cell fraction using 5-10 ul of 5 mM Tris/HCL pH 8.8/proteinase K cell lysis buffer overnight at 42° C. and then inactivation at 65° C. for 30 mins and 80° C. for 15 mins. The cell to buffer ratio was maintained at 10 µL buffer:2 cells. The number of cells lysed per sample is indicated in Table IV.

This was followed by a TaqMan real-time PCR (qPCR) assay with the Copy No. probe (Applied Biosystems) to validate the DNA extraction procedure and SRY probe (Applied Biosystems) to confirm the male gender of the isolated EVT (fetal samples).

For Targeted Sequencing:

The number of cells on the slides from samples is counted and the area with cells is marked. The coverslips on the FISH processed cells are separated by immersing them in 1×SSC buffer (at 75° C.) for 3 mins until the coverslip lifts off. The slide and the coverslip are then both visualized under the microscope, to determine if there was any cell loss.

The unstained slides are also viewed under bright field microscope to mark the area with cells. The slides are then immersed in freshly prepared protease solution (0.011 gm Pepsin in 0.01N HCl) for 11 min at 37° C. The slides are then washed 1×PBS (Phosphate buffered saline, pH 7.5) for 5 min at room temperature. The slides are then dehydrated by passing them through alcohol gradients ethanol 90%, 80% and 70% each for 1 min and allowed to dry. The slides are again viewed under the microscope again to ensure that there is no cell loss.

The cells are lysed by adding 5 µl of lysis buffer (Arcturus PicoPure DNA extraction kit, ThermoFischer) heated to 65° C. and the slide is placed on the thermocycler set at 65° C. for 1-2 min. An additional 5 µl of lysis buffer is added and the total amount is removed from the slide and placed in a 0.2 ml tube. The final amount of lysis buffer in the tube is adjusted to maintain a ratio of 2 cells/1 uL of buffer. The slide is visualized to ensure that all the cells have been extracted off the slide. The tubes are then incubated overnight at 65° C. followed by inactivation at 95° C. for 30 mins. The success of DNA isolation is confirmed by TaqMan real-time PCR (qPCR) assay with the Copy No. probe (Applied Biosystems) and SRY probe (Applied Biosystems) to confirm the gender.

TABLE IV

List of samples and corresponding number of cells lysed

| Sample No. | Cell No. |
|---|---|
| 0318-4A-(S5-F) | 27 |
| 0318-4A-(S5-M) | 20 |
| 1007-3A-(S2-F) | 25 |
| 1007-3A-(S2-M) | 20 |
| 1028-3B-(S3-F) | 25 |
| 1028-3B-(S3-M) | 20 |
| 0325-4A-(S4-F) | 13 |
| 0325-4A-(S4-M) | 20 |
| 0624-4A-(S1-F) | 27 |
| 0624-4A-(S1-M) | 20 |

Example 3

Isolation of Genomic DNA from Fetal Extravillous Trophoblast Cells

A maternal endocervical sample is collected using a cytobrush and the cytobrush is rinsed in ice-cold culture medium or PBS (137 mM NaCl, 10 mM Phosphate buffer).

Cells are centrifuged and resuspended in 10 ml PBS plus 2.7 mM $CaCl_2$, 1 mM $MgCl_2$ and then warmed to room temperature.

The magnetic separation procedure for removing fetal cells is started by addition of 20 ul of 250 nm magnetic nanoparticles conjugated to an anti-HLA-G antibody to the washed cells after resuspension in 1 ml PBS and incubated at 4° C. for 1 to 24 hours with shaking.

Maternal cells (HLA-G negative) are separated from magnetized (HLA-G positive) fetal extravillous trophoblast cells using a DynaMag™ Spin magnet (Life Technologies).

The fetal extravillous trophoblast cells are then washed 3 times using a magnet to remove residual maternal cells.

The isolated fetal extravillous trophoblast cells are resuspended in a solution of 50-100 microliters PBS/10 mM EDTA. An aliquot of 15 microliters is removed for cell counting and quality control for fetal cells. Optionally, the isolated maternal cells are resuspended in a solution of 50-100 microliters PBS/10 mM EDTA and an aliquot of 15 microliters is removed for cell counting and quality control, if desired.

The isolated fetal extravillous trophoblast cells are lysed by addition of 50 mM Tris-HCl, pH 8.5, 150 mM NaCl, 1% NP-40, followed by centrifugation at low speed, about 1000×g, to pellet intact fetal extravillous trophoblast cell nuclei. The supernatant is removed and the nuclei are washed with PBS/10 mM EDTA two or three times.

Genomic DNA is extracted from the fetal extravillous trophoblast cell nuclei by addition of 25 microliters of 3× concentrated DNA extraction buffer (90 mM TRIS, 90 mM EDTA, 1.5% EDTA, pH 8.0, 3 mg/ml Proteinase K) to 50 microliters of the isolated fetal extravillous trophoblast cell nuclei. The nuclei are then incubated for 3 hrs at 65° C., followed by 10 min at 95° C.

The extracted genomic DNA is frozen for subsequent assays or can be further purified by centrifugation at high speed in a microcentrifuge for 5 minutes. Optionally the DNA is still further purified, for example using commercial DNA purification and concentration kits, such as a Zymresearch DNA 10 concentration kit.

Example 4

Isolation of Genomic DNA from Fetal Extravillous Trophoblast Cells

A maternal endocervical sample is collected using a cytobrush by inserting it approximately 2 cm into the endocervical canal and rotating 2 or 3 times as it is withdrawn. Mucus present in the canal is also collected in the brush. The cytobrush is rinsed in fixative, for example, using a ThinPrep kit. The specimen is stored refrigerated or at ambient temperature and transported to the laboratory for further processing. It can be stored at 4° C. for at least one week without loss of RNA or HLA-G protein.

To isolate fetal extravillous trophoblast cell genomic DNA, all cells are washed twice with PBS after acidification of the maternal endocervical sample by adding 0.6 ml of acetic acid to the 20-ml volume of ThinPrep containing the cells, achieving a final concentration of 3% acetic acid.

The cells are centrifuged through a 250 micron filter and resuspended in 10 ml PBS at 4° C. The cells are then washed 2 more times in 10 ml PBS and the final pellet is brought to a volume of 1 ml in PBS.

The magnetic separation procedure for removing fetal cells is started by addition of 20 ul of 250 nm magnetic nanoparticles conjugated to an anti-HLA-G antibody to the washed cells after resuspension in 1 ml PBS and incubated at 4° C. for 1 to 24 hours with shaking.

Maternal cells (HLA-G negative) are separated from magnetized (HLA-G positive) fetal extravillous trophoblast cells using a DynaMag™ Spin magnet (Life Technologies).

The fetal extravillous trophoblast cells are then washed 3 times using a magnet to remove residual maternal cells.

The isolated fetal extravillous trophoblast cells are resuspended in a solution of 50-100 microliters PBS/10 mM EDTA. An aliquot of 15 microliters is removed for cell counting and quality control for fetal cells. Optionally, the isolated maternal cells are resuspended in a solution of 50-100 microliters PBS/10 mM EDTA and an aliquot of 15 microliters is removed for cell counting and quality control, if desired.

DNase I is prepared by dissolving 1 mg DNase I powder (Worthington Cat #2138, >2000 Kunitz units/mg) in 10 ml PBS plus 0.9 mM $MgCl_2$.

To protect nuclear DNA from degradation by nucleases entering the fixed, permeable isolated fetal extravillous trophoblast cells, the DNAse is attached, such as by covalent linkage, to one or more supports such as beads or particles that cannot penetrate the fixed cells. In this example, DNAse covalently bound to non-magnetic beads is added to the isolated fetal extravillous trophoblast cells, 5 microliters of F7 (MoBiTec, Germany), and incubated for 10 mins at room temperature.

The DNAse-treated isolated fetal extravillous trophoblast cells are centrifuged through a 250 micron filter and resuspended in 10 ml PBS at 4° C. The cells are then washed 2 more times in 10 ml PBS and the final pellet is brought to a volume of 1 ml in PBS. DNase immobilized on beads will be removed before fetal DNA extraction, using size exclusion methods such as gel filtration, filtration over meshes, laminar flow in microfluidic channels or other appropriate methods.

The DNAse-treated isolated fetal extravillous trophoblast cells are lysed by addition of 50 mM Tris-HCl, pH 8.5, 150 mM NaCl, 1% NP-40, followed by centrifugation at low speed to pellet intact fetal extravillous trophoblast cell nuclei. The supernatant is removed and the nuclei are washed with PBS/10 mM EDTA two or three times.

Genomic DNA is extracted from the fetal extravillous trophoblast cell nuclei by addition of 25 microliters of 3× concentrated DNA extraction buffer (90 mM TRIS, 90 mM EDTA, 1.5% EDTA, pH 8.0, 3 mg/ml Proteinase K) to 50 microliters of the isolated fetal extravillous trophoblast cell nuclei. The nuclei are then incubated for 3 hrs at 65° C., followed by 10 min at 95° C.

The extracted genomic DNA is frozen for subsequent assays or can be for further purified by centrifugation at high speed in a microcentrifuge for 5 minutes. Optionally the DNA is still further purified, for example using commercial DNA purification and concentration kits, such as a Zymresearch DNA 10 concentration kit.

Example 5

Samples

Maternal and fetal cells were isolated from endocervical specimens (n=22) obtained at gestational ages ranging from 5 to 19 weeks (9.1±4.0 weeks) and a corresponding newborn blood spot was obtained after delivery of each fetus. In a second group of women terminating pregnancy in the first trimester, endocervical specimens and matched placental tissue were obtained.

Isolation of Endocervical Fetal Trophoblast Cells

Endocervical samples were immediately fixed using a ThinPrep kit (Hologic, Marlborough, Mass.). The endocervical samples were centrifuged, re-suspended in 10 mL phosphate buffered saline (PBS), and then washed three times with PBS. After a final resuspension in 1.5 mL PBS, anti-HLA-G-coated magnetic nanoparticles were added and incubated overnight at 4° C. with mixing. The non-bound (maternal) cells were collected after magnetic immobilization and separation of HLA-G-positive (fetal) cells. Isolated cells of both types were then washed three times in PBS. Trophoblast cells (110-1515, average 373 from each sample) and maternal cells were counted, and groups of approximately 50 cells were mounted onto glass microscope slides. The cells were assessed by immunofluorescence microscopy for expression of β-hCG, and the percentage of labeled cells was determined. Expression of the trophoblast-specific protein, β-hCG was present in the isolated fetal cells in an average of 89.8±5.2% of the isolated fetal cells, while β-hCG was absent from isolated maternal cells. Table V shows examples from three of the samples that were assessed.

TABLE V

| Fetal and maternal DNA isolation and analysis by Exome Sequencing. | | | | | | |
|---|---|---|---|---|---|---|
| Sample ID | S1 | | S2 | | S3 | |
| Gestational Age | 5.2 wks | | 7 wks | | 14 wks | |
| Cell isolate (F/M)* | F | M | F | M | F | M |
| Trophoblast purity (% β-hCG) | 98 | 0 | 86 | 0 | 89 | 0 |

TABLE V-continued

Fetal and maternal DNA isolation and analysis by Exome Sequencing.

| Sample ID | | S1 | | S2 | | S3 | |
|---|---|---|---|---|---|---|---|
| FISH[1] (# cells with Y chr/total) | | Male (27/27) | | Male (13/13) | | Male (25/25) | |
| qPCR Ct values | SRY | 36.9 | | 39.0 | | 37.1 | |
| | RNase H | 35.1 | 34.0 | 36.5 | 34.7 | 28.8 | 26.6 |
| Exome Sequencing Results | | | | | | | |
| Aligned reads (%) | | 99.5 | 99.3 | 85.5 | 99.4 | 99.3 | 98.8 |
| Median sequencing depth | | 157 | 133 | 205 | 269 | 167 | 141 |
| Variant Analysis | | | | | | | |
| Comparison between F & M | # Total shared variants | 589 | | 124 | | 398 | |
| | # Informative variants (%) | 160 (27.2) | | 46 (37.1) | | 65 (16.3) | |

Fluorescence In Situ Hybridization (FISH)

Isolated fetal extravillous trophoblast cells were mounted on slides and probed for X and Y chromosomes by FISH using the DYZ1 satellite III on the Y chromosome, and the DXZ1 alpha satellite on the X chromosome as fluorescently-labeled probes (Abbott Molecular). Nuclei were counterstained with DAPI and scored for each chromosome to quantify cells that were XX or XY. Fluorescence in situ hybridization (FISH) for the X and Y chromosomes and quantitative PCR (qPCR) for the SRY gene identified trophoblast isolates from male fetuses.

DNA Extraction and Isolation from Isolated Nuclei

Fetal DNA was obtained by isolation of fetal extravillous trophoblast nuclei prior to extracting fetal DNA from the nuclei. Isolated fetal extravillous trophoblast cells were mounted on slides, lysed, and fetal cell DNA was extracted from nuclei which remained attached to the slides.

The cells were lysed to release intact nuclei by incubation in freshly prepared protease solution (0.011 gm pepsin in 100 mL 0.01N HCl) for 11 min. at 37° C. to lyse the cells and release intact fetal extravillous trophoblast nuclei.

The nuclei were lysed by incubation in 5-10 ul of 5 mM Tris/HCL pH 8.8/proteinase K cell lysis buffer overnight at 42° C. and the cell to buffer ratio was maintained at 1 µL buffer:2 cells. After inactivation at 65° C. for 30 mins and 80° C. for 15 mins, 1 µl µL was used for qPCR of RNaseH and SRY genes to confirm DNA extraction from the nuclei and the male gender of the fetal cells.

The corresponding maternal cell DNA was extracted from 20-cell aliquots of maternal cells from the corresponding endocervical samples, depleted of fetal cells by immunomagnetic separation, that had been stored frozen in PCR tubes.

DNA Extraction and Isolation from Isolated Nuclei after DNase Digestion

Targeted sequencing was performed on DNA isolated from cells treated with DNAse. Fetal and maternal cells isolated from endocervical samples were dropped on separate slides and allowed to dry, adhering them to the slides.

The slides with adhered fetal cells were immersed in freshly prepared protease solution (0.011 gm pepsin in 100 mL 0.01N HCl) for 11 min at 37° C. to lyse the cells and release intact fetal extravillous trophoblast nuclei, followed by a PBS wash for 5 mins to remove cell plasma membranes and potential maternal DNA fragments, producing isolated fetal extravillous trophoblast nuclei. Exogenous DNA (i.e. non-fetal DNA) was further eliminated from the glass-bound isolated fetal extravillous trophoblast nuclei by adding 10 µL of washed, immobilized DNase (DNase I, immobilized on matrix F7M, MoBiTec, Goettingen, Germany) onto the pepsin-treated slides, and incubating for 3-5 mins at room temperature. The slides were washed with PBS to terminate DNAse activity by removing the DNAse-containing beads.

The isolated fetal extravillous trophoblast nuclei were then lysed by incubation overnight at 65° C. with 0.5 µL/cell 5 mM Tris/HCL pH 8.8/proteinase K nuclei lysis buffer overnight at 42° C. and the cell to buffer ratio was maintained at 1 µL buffer:2 cells. The protease was then inactivated by incubation at 95° C. for 30 min.

The maternal cells adhered to slides were lysed by incubation overnight at 65° C. with 0.5 µL/cell 5 mM Tris/HCL pH 8.8/proteinase K nuclei lysis buffer overnight at 42° C. and the cell to buffer ratio was maintained at 1 µL buffer:2 cells. The protease was then inactivated by incubation at 95° C. for 30 min. For maternal cells, nuclei were not isolated prior to DNA extraction and no DNAse treatment of the cells was performed.

Placental villi (20-25 mg) were dissected and suspended in 100 µL PBS. Ten µL of immobilized DNase was added and shaken for 10 min at room temperature to ensure efficient DNA digestion. DNase beads were removed by washing in PBS. DNA was extracted from the tissue, using a standard DNA isolation method.

All DNA was purified using the Qiagen MinElute PCR purification kit, eluted in a final volume of 20 µL, and quantified using a fluorescent DNA assay.

Reference DNA Extraction and Isolation from Blood and Tissue

Two mL of maternal blood was layered onto a 5 mL Ficoll-Hypaque solution (GE Healthcare) and centrifuged at 200×g for 10 min before collecting the leukocyte layer (buffy coat). Newborn blood spots were obtained as ¼-inch punches from blood spots on collection cards. DNA was extracted from the maternal buffy coat and newborn blood spots, using the EZ1 DNA Blood Kit (Qiagen) and the EZ1 DNA Investigator Kit (Qiagen), respectively, according to the manufacturers' protocols. DNA was purified, using the MiniElute PCR purification kit (Qiagen), following manufacturer's protocol. As an alternative to maternal blood, DNA from 10,000 maternal cells isolated from the endocervical samples was extracted, using a standard silica column based DNA purification protocol, commercially available as DNeasy Blood & Tissue Kit (Qiagen). All isolated DNA was quantified using a fluorescent DNA intercalating dye assay, Pico Green Assay (Invitrogen).

Quantitative PCR (qPCR)

The sex of each fetus was determined by multiplex, real-time qPCR with TaqMan probes and primers for RNaseH and male SRY genes (Life Technology), using a BioRad CFX 364 real-time fluorescence thermocycler with automated data analysis. Samples were incubated at 95° C. for 10 mins before 50 cycles at 92° C. for 15 sec and 60° C. for 1 min.

Whole Genome Amplification (WGA)

Fetal genomic DNA was isolated from 10-50 nuclei, see Table V, and aliquots of fetal or maternal DNA (~4 genome equivalents) were used for whole genome amplification (WGA). WGA was confirmed by PCR amplification of four autosomal chromosome fragments, see FIGS. 1 and 2. A portion of DNA (approximately 4 copies) isolated from the fetal and maternal cells was subjected to PCR-based WGA, Ampli 1™ Whole Genome Amplification Kit (Silicon Biosystems) which provides balanced and complete amplification of the entire genome of a cell, following the manufacturer's protocol. This was followed by a 3x bead purification using a standard commercial solid phase reverse immobilization bead-based purification system, Agencourt Ampure XP paramagnetic beads. DNA binds, due to its charge to functional groups on the beads. Proteins have less affinity to beads and are washed away using the manufacturer's protocol.

To evaluate the quality of the WGA procedure, a 6-μL aliquot of each amplified sample was assessed by 1% agarose gel electrophoresis, see FIG. 1, and using a PCR-based assay which amplifies selected regions, Amplifi 1™ QC kit (Silicon Biosystems). The results were evaluated, using gel electrophoresis to compare the bp length of the QC assay amplicons with those expected as per the kit, see FIG. 2. Each sample was amplified in triplicate and individual replicates were assessed for quality. The replicates were pooled for DNA library preparation.

Library Preparation for Exome Sequencing

Both WGA amplified DNA (from nuclei of fetal trophoblast cells isolated from endocervical samples, maternal endocervical cells isolated from endocervical samples) and unamplified DNA (from newborn blood spots and maternal cells or blood) was sequenced. DNA libraries were prepared using the Nextera Rapid Capture Exome Kit (Illumina) with 50 ng of input DNA, following the manufacturer's protocol. Uniquely barcoded adaptors were ligated to samples, followed by PCR amplification and library purification. The final library pool was quantified, and its quality assessed using high-sensitivity DNA Chips (Agilent Technologies, see FIG. 3.

Each library was quantified by RT-PCR, using the KAPA library quantification kit (KAPA Biosystems—Illumina). The DNA standards provided in the kit represent a 10-fold dilution series from 0.0002 to 20 pM. Two nM of each individual library were combined for multiplex sequencing, which eliminated sequencing lane effects. The libraries were sequenced in a rapid flow cell on an Illumina HiSeq 2500.

Exome Sequencing Data Analysis

Alignment and variant calling of the exome sequencing reads was performed using the BWA Enrichment pipeline version 2.1.0.0 (Illumina BaseSpace Workflow), with the Homo Sapiens reference genome (UCSC hg19), targeted regions of the Nextera Rapid Capture Exome v1.2, including trimming of adaptors and flagging of PCR duplicates. VCF files were subsequently loaded into Illumina Variant Studio 2.2 to filter calls that passed the BWA Enrichment quality control, ensure a minimum read depth of 100, and remove insertion and deletion variants.

Variants shared between each maternal and fetal pair were identified, followed by filtering out of shared homozygotes and shared heterozygotes, using a variant allele percentage>85 to be considered a homozygote, and a variant allele percentage<85 to be considered a heterozygote. Secondly, the minimal difference between the maternal and fetal variant allele percentage was set at 25. The remaining variants were considered informative, i.e. maternal homozygote/fetal heterozygote, or maternal heterozygote/fetal homozygote.

For variants shared between WGA-amplified and unamplified samples of the same individual, allele dropout was identified when unamplified DNA showed heterozygosity, while amplified DNA showed homozygosity. Additional alleles were identified in WGA-amplified DNA that were heterozygous, while unamplified samples were homozygous.

Chromosomal coverage ratios were determined by calculating the mean coverage value per chromosome for each targeted region as a ratio of diploid chromosome coverage.

Sequencing data, shown in Tables VI and VII, revealed coverage of all chromosomes.

TABLE VI

Exome sequencing of WGA (Fetal and maternal) products for three samples

| Sample ID | S1 WGA | | S2 WGA | | S3 WGA | |
| --- | --- | --- | --- | --- | --- | --- |
| | Maternal | Fetal | Maternal | Fetal | Maternal | Fetal |
| General analysis information | | | | | | |
| Total reads (Illumina filter passed) | 3.840E+07 | 2.073E+07 | 1.545E+07 | 2.106E+08 | 4.598E+07 | 1.183E+07 |
| Quality score Q30 (%) | 90.7 | 92.0 | 86.8 | 84.0 | 90.8 | 91.6 |
| Read enrichment (%) | 70.1 | 67.9 | 69.7 | 62.0 | 66.8 | 55.5 |
| Padded read enrichment (%) (padding size 150 bp) | 72.5 | 70.1 | 72.1 | 67.3 | 70.8 | 59.1 |
| Duplicate paired reads (%) | 10.0 | 5.9 | 41.2 | 43.9 | 9.6 | 6.1 |
| Fragment length median ± SD | 123 ± 64 | 121 ± 62 | 130 ± 67 | 171 ± 84 | 144 ± 82 | 144 ± 83 |

TABLE VI-continued

Exome sequencing of WGA (Fetal and maternal) products for three samples

| | | S1 WGA | | S2 WGA | | S3 WGA | |
|---|---|---|---|---|---|---|---|
| Sample ID | | Maternal | Fetal | Maternal | Fetal | Maternal | Fetal |
| Variant analysis | | | | | | | |
| Total # variants after applied filters | | 5,577 | 1,466 | 661 | 8,850 | 6,928 | 988 |
| Range sequencing depth (100-. . .) | | 1,681 | 839 | 4,385 | 9,886 | 2,934 | 1,150 |
| Comparison with Unamplified samples | # Shared variants | 174 | 5267 | 843 | 37 | 107 | 2507 |
| | # Allele dropouts (%) | 16 (9.2) | 93 (1.8) | 166 (19.7) | 14 (37.8) | 6 (5.6) | 494 (19.7) |
| | # De Novo Allele (%) | 11 (6.3) | 10 (0.2) | 70 (8.3) | 1 (2.7) | 6 (5.6) | 286 (11.4) |

TABLE VII

Exome sequencing of unamplified (maternal blood and neonatal blood spot) DNA for three samples

| | S1 Unamplified | | S2 Unamplified | | S3 Unamplified | |
|---|---|---|---|---|---|---|
| Sample ID | Maternal | Fetal | Maternal | Fetal | Maternal | Fetal |
| General analysis information | | | | | | |
| Total reads (Illumina filter passed) | 1.618E+08 | 2.172E+07 | 3.169E+07 | 4.523E+07 | 1.142E+08 | 3.029E+07 |
| Quality score Q30 (%) | 88.8 | 90.5 | 90.3 | 90.4 | 89.6 | 91.1 |
| Aligned reads (%) | 99.3 | 99.8 | 99.8 | 99.8 | 99.5 | 99.8 |
| Read enrichment (%) | 70.3 | 67.8 | 66.0 | 63.7 | 72.1 | 68.6 |
| Padded read enrichment (%) (padding size 150 bp) | 73.0 | 72.0 | 71.0 | 68.2 | 73.7 | 70.9 |
| Duplicate paired reads (%) | 19.0 | 4.5 | 5.7 | 4.9 | 19.3 | 5.1 |
| Fragment length median ± SD | 117 ± 60 | 143 ± 80 | 156 ± 85 | 143 ± 78 | 100 ± 48 | 113 ± 57 |
| Variant analysis | | | | | | |
| Total # variants after applied filters | 24,797 | 1,089 | 2,174 | 3,848 | 14,837 | 1,246 |
| Median sequencing depth | 181 | 131 | 130 | 127 | 156 | 123 |
| Range sequencing depth (100-. . .) | 2,134 | 1,432 | 1,741 | 1,629 | 2,488 | 1,027 |

Figure 4:
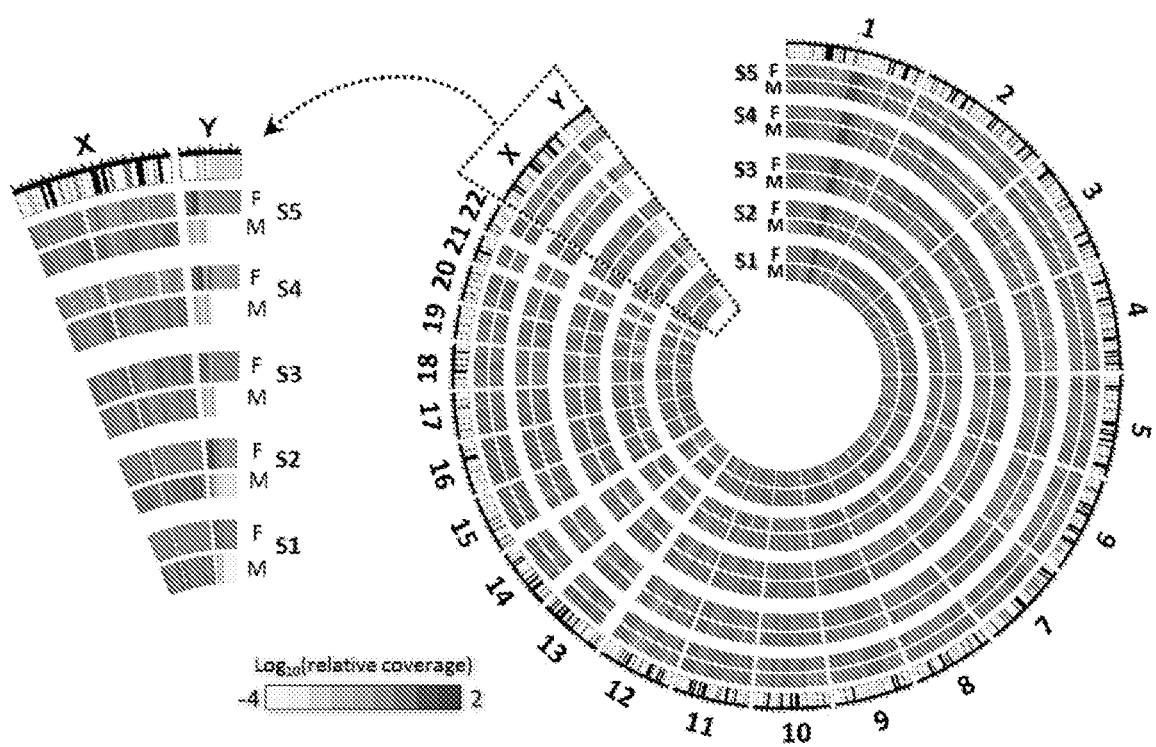
FIG. 4 is an image of a Cercos heat map that indicates mean coverage by targeted regions (~1 Mb) of all exome sequences on log 10 scale, indicating each chromosome (1-22, X, Y) in maternal (M) and fetal (F) samples; the expanded region on the left shows detailed coverage for X and Y chromosomes.
Figure 5A:
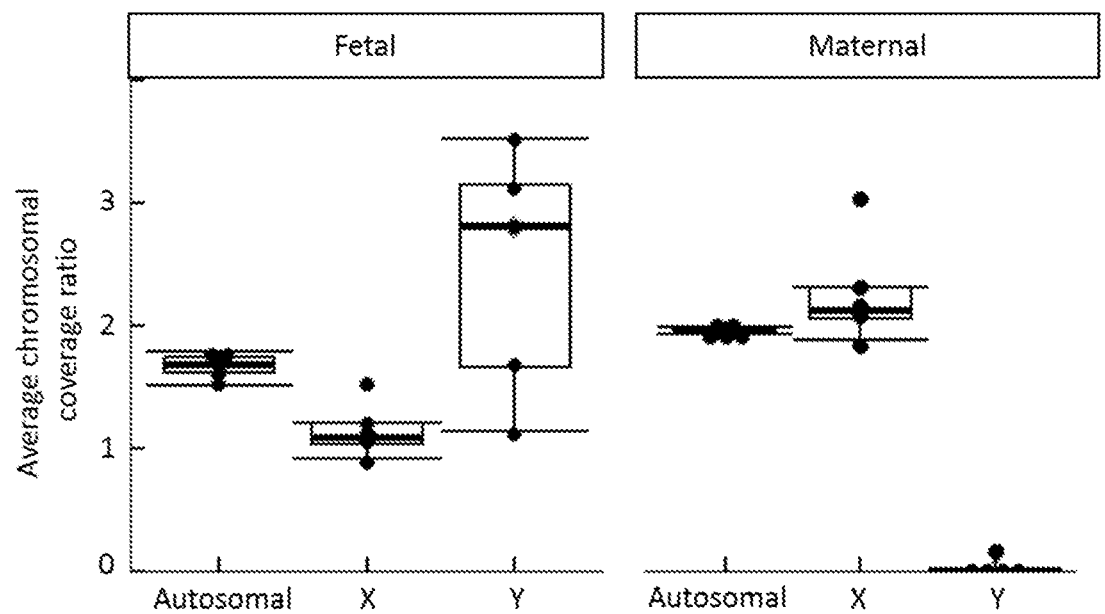
FIG. 5A is a graph showing the relative coverage of autosomal, X and Y chromosomes after WGA for fetal and maternal cells.
Figure 5B:
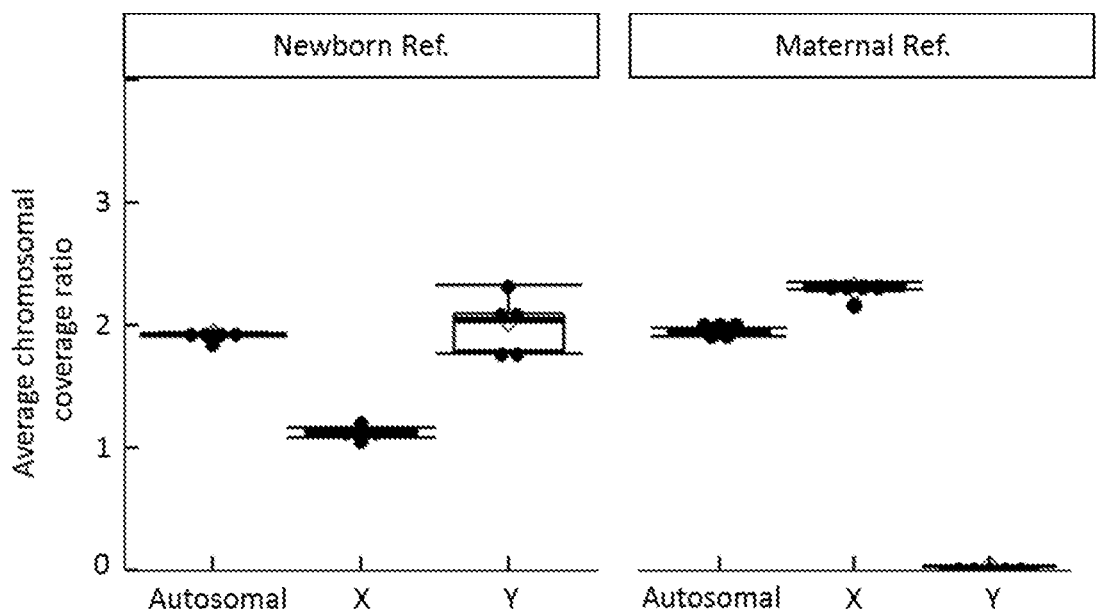
FIG. 5B is a graph showing the relative coverage of autosomal, X and Y chromosomes after WGA for newborn blood samples (bloodspots) and maternal blood samples which are used reference standards.

Coverage of all chromosomes is also shown by results presented in FIG. 4. FIG. 4 is a Cercos heat map that indicates mean coverage by targeted regions of all exome sequences on a $\log_{10}$ scale, indicating each chromosome (1-22, X, Y) in maternal (M) and fetal (F) samples. Higher coverages are indicated by darker gray color. The outermost circle represents the chromosome ideograms with the pter-qter orientation in a clockwise direction and the centromeres in black. The expanded region (left) shows detailed coverage for X and Y chromosomes. FIG. 5A shows the relative coverage of autosomal, X and Y chromosomes after WGA for the fetal and maternal cells, and FIG. 5B shows the relative coverage of autosomal, X and Y chromosomes after WGA for newborn blood samples (blood spots) and maternal blood samples, which are used as reference standards. The dots in FIGS. 5A and 5B represent individual data points; Boxes: 25th to 75th percentiles; horizontal lines within the boxes: median; whiskers: 1.5×Inter Quartile Range (3rd quartile−1st quartile). Consistent with their respective female and male genders, the expected ratio of autosomal:X:Y chromosomes in maternal DNA (2:2:0) was obtained (1.96±0.03 to 2.29±0.46 to 0.05±0.08), while the expected ratio for a male fetus (2:1:1) was obtained (1.67±0.11 to 1.16±0.24 to 2.46±1.02) in trophoblast DNA from isolated fetal nuclei, see FIG. 5A. The elevated proportion of Y chromosome in trophoblast cells was most likely due to incorrect alignment, because much of the Y chromosome is shared with the X chromosome. WGA amplified DNA, see FIG. 5A, showed larger variations in chromosomal coverage than unamplified DNA, see FIG. 5B, due to preferential amplification of non-GC-rich regions during WGA.

Example 6

Targeted Sequencing

DNA was obtained from nuclei of fetal trophoblast cells isolated from endocervical samples, maternal endocervical cells isolated from endocervical samples and tissue from the corresponding placenta as described above for exome sequencing. Targeted sequencing was performed using pregnancies with both male and female fetuses (N=20).

Library Preparation for ForenSeq Targeted Sequencing

Fetal DNA from isolated nuclei of fetal trophoblast cells from endocervical samples or maternal endocervical cells isolated from endocervical samples (approximately 282 cells in 20 endocervical specimens ranging from 5 to 19 weeks gestational age, Table VIII), was sequenced and compared to sequenced reference fetal DNA isolated from matched placental specimens.

Individual samples were quantified by Qubit, and analyzed using Agilent high-sensitivity DNA chips prior to library normalization. The percentage of libraries between 200-1000 bp was calculated based on the library traces and was mixed accordingly at the core facility. A pool size of 200-1 kb was selected, and the size-selected negative controls were mixed into the pool. The samples were sequenced on a MiSeq FGX system including positive and negative controls (Illumina).

ForenSeq Targeted Sequencing Data Analysis

ForenSeq Targeted sequencing data was extracted from the ForenSeq Universal Analysis software, which provides a run quality report and detailed genotype. From this report, data was extracted and allele percentages determined, using the read depth of each Short Tandem Repeat (STR) or Single Nucleotide Polymorphism (SNP). For STR data, the two dominant alleles with highest relative peaks were used for further analysis.

To determine the purity of fetal DNA obtained from isolated fetal nuclei of fetal trophoblast cells isolated from endocervical samples, the level of contamination with maternal DNA was calculated from the SNP and STR data. For each sample triad (fetal, maternal, placental), the homo- or heterozygosity of each SNP was determined, first in the placenta, then comparing to fetal, and the percentage devia-

TABLE VIII

Overview of samples and results for targeted sequencing

| Sample ID | Gestational Age (weeks) | Trophoblast cell purity (% β-hCG) | Fetal Gender | Autosomal STR alleles in TRIC | | % Fetal Fraction (% maternal fraction) | Number of SNV's in Fetal trophoblast cells after threshold that were called Correctly (% total number of SNV's) | called Incorrectly |
|---|---|---|---|---|---|---|---|---|
| | | | | Median | Range | | | |
| $S_A$ | 5 | 86 | Male | 94.8 | 85.6-100 | 97.6 (2.4) | 93 (98.9) | 0 |
| $S_B$ | 5 | 89 | Female | 85.5 | 75.1-100 | 92.2 (7.8) | 77 (81.9) | 0 |
| $S_C$ | 5 | 91 | Female | 89.1 | 73.5-100 | 87.2 (12.8) | 82 (87.2) | 0 |
| $S_D$ | 6 | 85 | Female | 91.9 | 80.8-98.7 | 95.2 (4.8) | 89 (94.7) | 0 |
| $S_E$ | 6 | 92 | Male | 86.4 | 85.7-96.9 | 85.6 (14.4) | 62 (66.0) | 0 |
| $S_F$ | 6 | 93 | Male | 88.1 | 73.2-99.4 | 75.6 (24.4) | 55 (58.5) | 0 |
| $S_G$ | 6 | 89 | Male | 93.3 | 84.9-100 | 93.9 (6.1) | 91 (96.8) | 0 |
| $S_H$ | 6 | 86 | Female | 92.7 | 77.8-98.5 | 98.6 (1.4) | 89 (94.7) | 0 |
| $S_I$ | 6 | 89 | Male | 95 | 88.9-100 | 100 (0.0) | 90 (95.7) | 0 |
| $S_J$ | 7 | 92 | Female | 89 | 77.7-96.6 | 82.1 (17.9) | 68 (72.3) | 0 |
| $S_K$ | 8 | 80 | Female | 89 | 72.3-100 | 82.4 (17.6) | 74 (78.7) | 0 |
| $S_L$ | 8 | 96 | Female | 92 | 79.6-99.4 | 97.2 (2.8) | 87 (92.6) | 0 |
| $S_M$ | 8 | 96 | Female | 90.2 | 78.3-100 | 90.8 (9.2) | 91 (96.8) | 0 |
| $S_N$ | 8.4 | 92 | Female | 93.3 | 76.5-99.2 | 92.8 (7.2) | 90 (95.7) | 0 |
| $S_O$ | 9 | 85 | Male | 93.6 | 79.8-100 | 92.9 (7.1) | 90 (95.7) | 0 |
| $S_P$ | 9 | 94 | Male | 91.9 | 81.9-100 | 100 (0.0) | 92 (97.9) | 0 |
| $S_Q$ | 11 | 85 | Female | 91.9 | 73.8-97.6 | 95.9 (4.1) | 89 (94.7) | 0 |
| $S_R$ | 13 | 91 | Male | 87.4 | 77.7-100 | 91.9 (8.1) | 77 (81.9) | 0 |
| $S_S$ | 14 | 90 | Male | 91.7 | 81.8-100 | 92.6 (7.4) | 93 (98.9) | 0 |
| $S_T$ | 19 | 80 | Female | 93.2 | 85.3-99.5 | 98.7 (1.3) | 92 (97.9) | 0 |

Sequence analysis was completed 5-7 days after endocervical sampling. Approximately 1.9±0.9 ng DNA of each type was sequenced, using a ForenSeq DNA Signature Prep kit (Illumina) for targeted PCR and DNA library preparation, followed by analysis on the MiSeq FGx system. DNA libraries were prepared with the ForenSeq DNA Signature Prep Kit (Illumina), using "primer mix A" which allows analysis of 94 SNP loci and 59 STR loci (autosomal & sex chromosome specific), as instructed by the manufacturer.

tion of the fetal DNA was calculated. Deviations from homo- or heterozygosity were also calculated in the SNP profile of maternal DNA to determine a threshold of technical and/or biological variation. Maternal and placental SNP profiles were then compared, and the non-informative SNPs (i.e., identical maternal and placental alleles) were filtered out. For the informative SNPs, the deviations obtained from the maternal sample were subtracted from the fetal sample and multiplied by two (to account for two maternal alleles contributing to the fetal sample), yielding the percentage of maternal contamination.

To investigate whether STR genotypes alone could determine fetal DNA purity, each autosomal STR was used. The dominant alleles with highest relative peaks were summed, to establish the median and range, which discriminated the pure (<15% contamination) from impure samples. Pure samples had median STR alleles>85%, while impure samples had median STR alleles<80%. To establish a cutoff for discriminating pure from impure samples, 82.5% was chosen.

Figure 6:
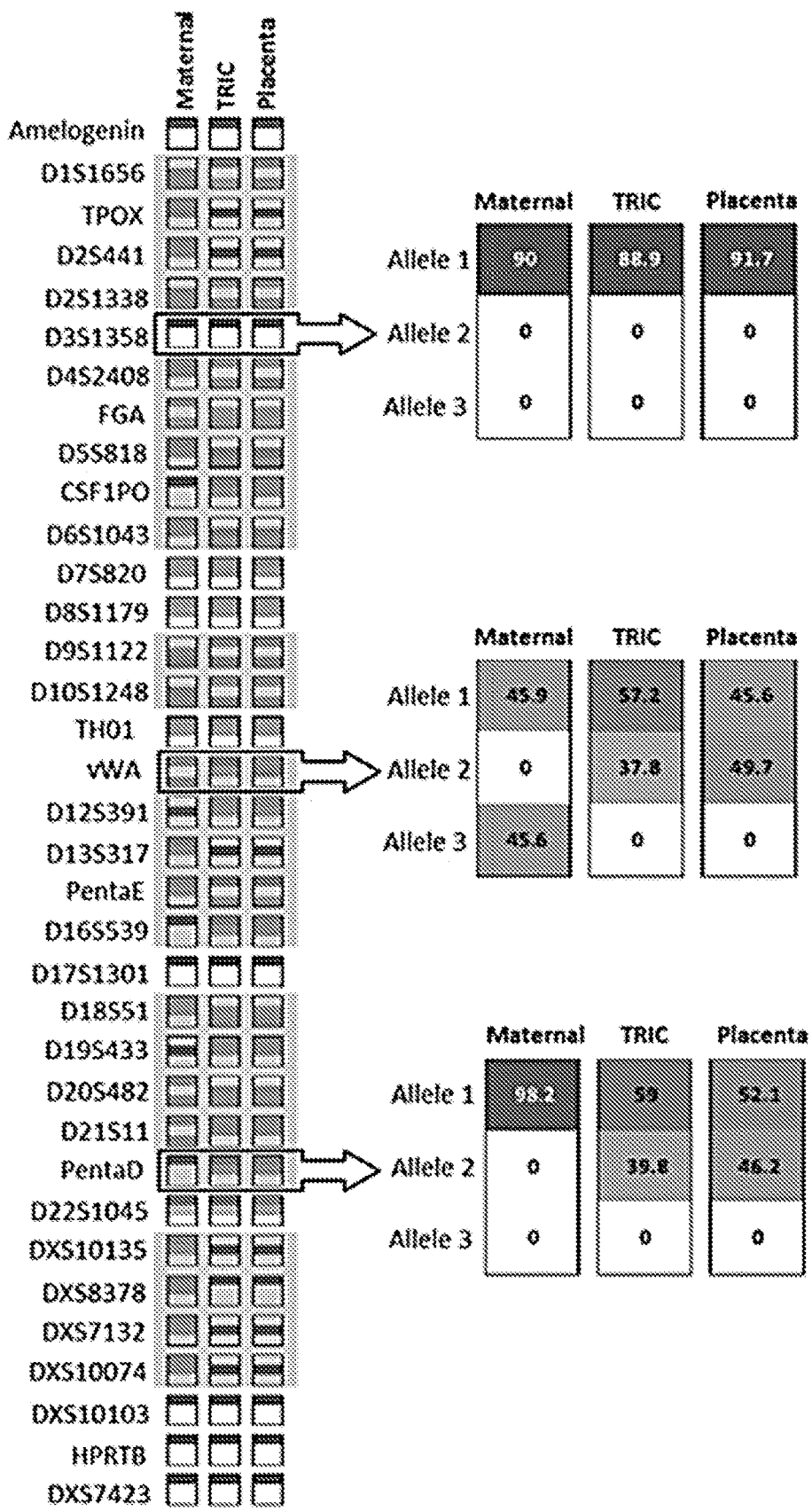
FIG. 6 is a graphical short tandem repeat (STR) profile of DNA obtained from maternal cells (Maternal), fetal trophoblast cells (TRIC), and placental tissue (Placenta) from one patient.

All 153 loci were successfully sequenced. Discriminatory SNP analysis revealed an average fetal DNA purity of 89.2±5.0%, see Table VIII, in fetal DNA obtained from isolated fetal trophoblast nuclei. In contrast to previous attempts to analyze fetal DNA isolated from cells shed from the placenta without isolating the fetal nuclei before DNA isolation, assay of fetal DNA from isolated trophoblast nuclei generated high-resolution STR profiles, detailing multiple shared and discriminatory alleles. A graphical STR profile of DNA triads composed of maternal cells (Maternal), fetal trophoblast cells (TRIC), and placental tissue (Placenta) from one sample is shown in FIG. 6. For each DNA sample, the two dominant alleles with highest relative peaks, or single peak when homozygous, were determined for each STR and compared among the triad. The adjacent mini-plots show distribution of shared STRs (upper mini-plot) and discriminatory STRs (middle and lower mini-plots) with the percentage of reads indicated numerically and by shade intensity for each dominant allele.

These data revealed concordance between allelic profiles of fetal DNA obtained from isolated nuclei of fetal trophoblasts obtained by TRIC and reference placental DNA, which were both distinct from maternal DNA, and provided 100% correct fetal gender identification in all samples, see Table VIII.

Figure 7:
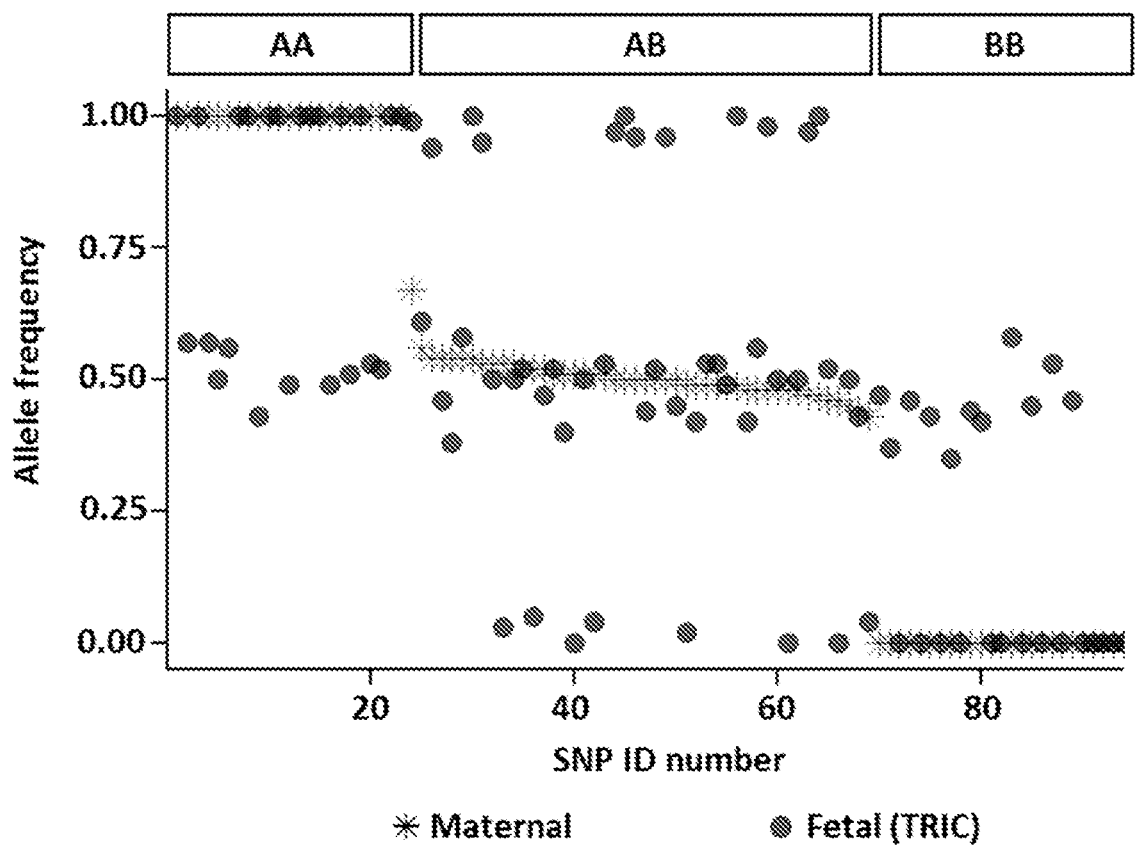
FIG. 7 is a graph showing a comparison of allelic frequencies for the 94 sequenced SNPs in corresponding maternal and fetal (TRIC) specimens for a single patient.
Figure 8:
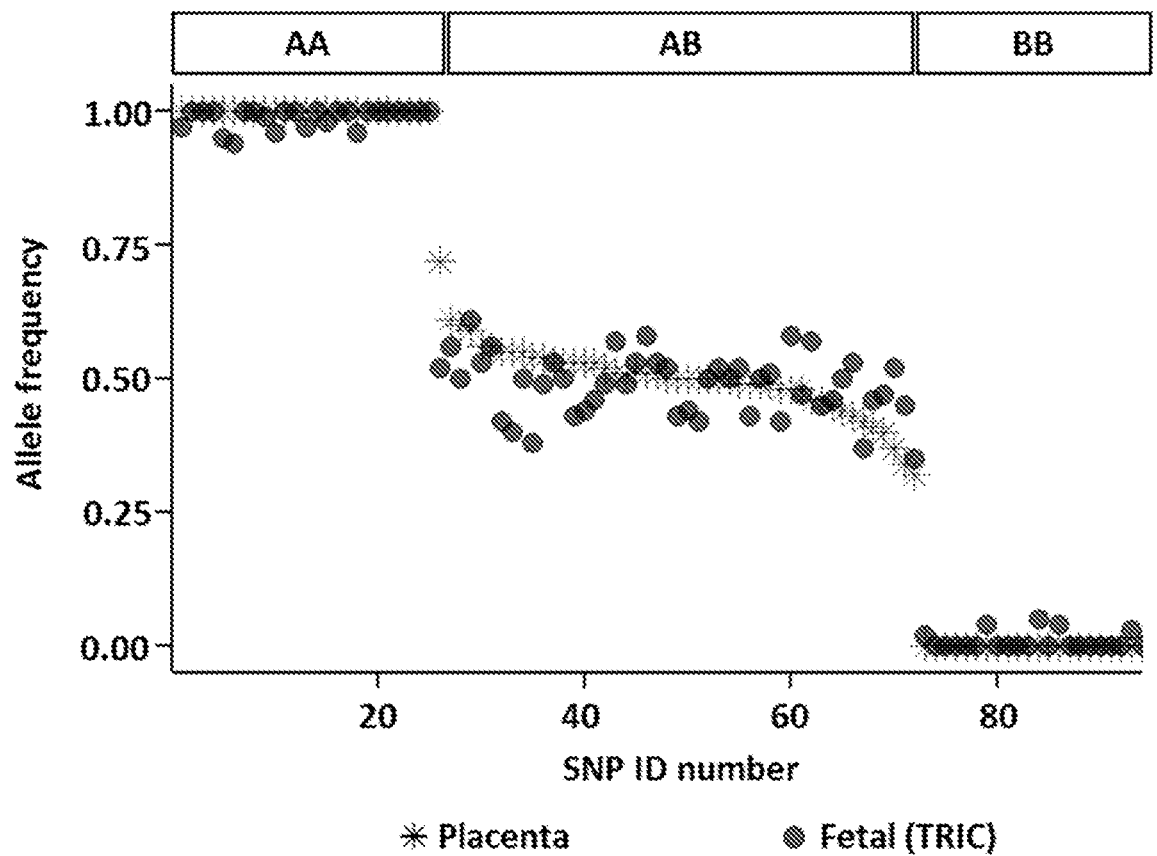
FIG. 8 is a graph showing a comparison of allelic frequencies for the 94 sequenced SNPs in corresponding fetal (TRIC) and placental specimens for a single patient.
Figure 9:
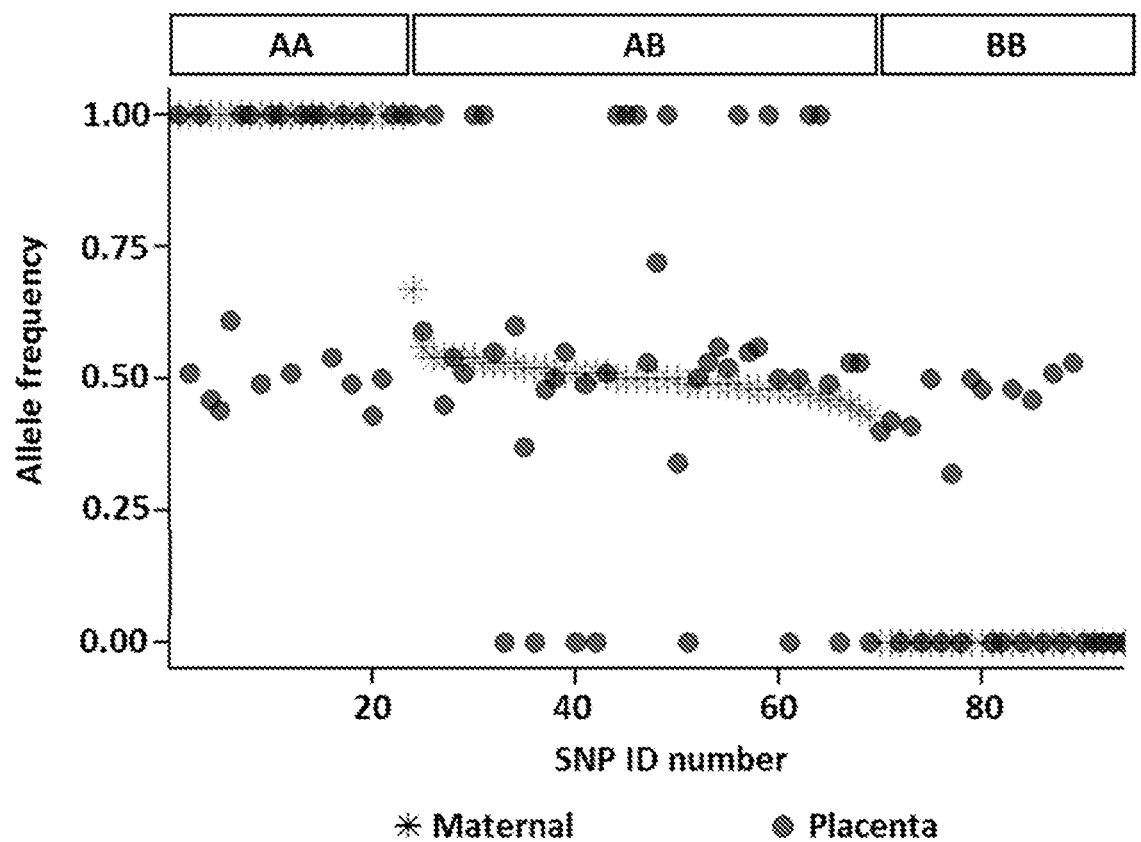
FIG. 9 is a graph showing a comparison of allelic frequencies for the 94 sequenced SNPs in corresponding maternal and placental specimens for a single patient.

Informative SNPs were identified (homozygote in maternal or fetal DNA, heterozygote in the other) by comparing the maternal genotype to the reference placental genotype, which was concordant with the fetal genotype. FIGS. 7, 8 and 9 show comparisons of allele frequencies for the 94 sequence SNPs in an example of the corresponding maternal, fetal (TRIC) and placental specimens for a single patient.

Informative SNPs were on average 48.7±5.5% of total SNPs. All maternal and fetal genotype pairs lacked forbidden combinations (AA/BB) at any allele, FIG. 7, consistent with unique individuals, related as parent and offspring. Comparison of the fetal (TRIC) DNA to DNA obtained from the corresponding placenta demonstrated genetic identity, see FIG. 8, while comparison of SNPs from maternal and placental DNA, shown in FIG. 9 revealed differences similar to those shown in FIG. 7.

Items

Item 1. A method of isolating DNA of a fetus of an ongoing pregnancy, comprising: obtaining a maternal endocervical sample containing maternal cells and fetal extravillous trophoblast cells from a pregnant subject; isolating fetal extravillous trophoblast cells from the maternal endocervical sample, producing isolated fetal extravillous trophoblast cells contaminated with maternal DNA; lysing the isolated fetal extravillous trophoblast cells; isolating fetal nuclei from the lysed fetal extravillous trophoblast cells, producing isolated fetal nuclei, thereby removing at least a portion of the contaminating maternal DNA; lysing the isolated fetal nuclei; and purifying genomic DNA from the isolated fetal nuclei, producing purified fetal genomic DNA.

Item 2. The method of item 1, further comprising treating the isolated fetal nuclei to remove at least a portion of the contaminating maternal DNA.

Item 3. The method of item 1 or 2, further comprising treating the isolated fetal nuclei with a DNAse prior to lysing the isolated fetal nuclei, thereby removing at least a portion of the contaminating maternal DNA.

Item 4. The method of any of items 1-3, further comprising treating the isolated extravillous trophoblast cells with a DNAse prior to isolating fetal extravillous trophoblast cells from the maternal endocervical sample, thereby removing at least a portion of the contaminating maternal DNA.

Item 5. The method of any of items 1-4, further comprising treating the isolated extravillous trophoblast cells with a DNAse prior to lysing isolated fetal extravillous trophoblast cells, thereby removing at least a portion of the contaminating maternal DNA.

Item 6. The method of any of items 1-5, wherein the fetal extravillous trophoblast cells are fixed prior to treating the fetal extravillous trophoblast cells with the DNAse and the DNAse is attached to a support, preventing entry of the DNAse into the fetal extravillous trophoblast cells.

Item 7. The method of any of items 1-5, wherein the fetal extravillous trophoblast cells are not fixed prior to treating the fetal extravillous trophoblast cells with the DNAse.

Item 8. The method of any of items 1-7, wherein the purified fetal genomic DNA is characterized by a fetal fraction in the range of 10%-100%.

Item 9. The method of any of items 1-8, wherein the purified fetal genomic DNA is characterized by a fetal fraction in the range of 25%-100%.

Item 10. A method of assaying DNA of a fetus of an ongoing pregnancy, comprising: obtaining a maternal endocervical sample containing fetal extravillous trophoblast cells from a pregnant subject; isolating fetal extravillous trophoblast cells from the maternal endocervical sample; lysing the isolated fetal extravillous trophoblast cells; isolating fetal nuclei from the lysed fetal extravillous trophoblast cells; lysing the isolated fetal nuclei and purifying genomic DNA from the isolated fetal nuclei; and assaying the purified fetal genomic DNA, thereby determining a characteristic of a genomic DNA sequence of the purified fetal genomic DNA, and thereby assaying genomic DNA of a fetus of an ongoing pregnancy.

Item 11. The method of item 10, wherein assaying the purified fetal genomic DNA determines a characteristic of at least one individual nucleotide in a genomic DNA sequence of the purified fetal genomic DNA, thereby assaying DNA of a fetus of an ongoing pregnancy with single base resolution.

Item 12. The method of item 10 or 11, wherein the assaying comprises a method selected from the group consisting of: sequencing, high resolution melt analysis, methylation analysis, capillary electrophoresis, mass spectrometry, single strand conformation polymorphism, single base extension, restriction fragment length polymorphism.

Item 13. The method of any of items 10-12, wherein the sequencing comprises a method selected from the group consisting of: massively parallel signature sequencing, single-molecule real-time sequencing, polony sequencing, ion semiconductor, pyrosequencing, sequencing by synthesis, sequencing by ligation and chain termination sequencing.

Item 14. The method of any of items 10-13, further comprising treating the isolated fetal nuclei to remove at least a portion of the contaminating maternal DNA.

Item 15. The method of any of items 10-14, further comprising treating the isolated fetal nuclei with a DNAse prior to lysing the isolated fetal nuclei, thereby removing at least a portion of the contaminating maternal DNA.

Item 16. The method of any of items 10-15, further comprising treating the isolated extravillous trophoblast cells with a DNAse prior to isolating fetal extravillous trophoblast cells from the maternal endocervical sample, thereby removing at least a portion of the contaminating maternal DNA.

Item 17. The method of any of items 10-16, further comprising treating the isolated extravillous trophoblast cells with a DNAse prior to lysing isolated fetal extravillous trophoblast cells, thereby removing at least a portion of the contaminating maternal DNA.

Item 18. The method of any of items 10-17, wherein the fetal extravillous trophoblast cells are fixed prior to treating the fetal extravillous trophoblast cells with the DNAse and the DNAse is attached to a support, preventing entry of the DNAse into the fetal extravillous trophoblast cells.

Item 19. The method of any of items 10-17, wherein the fetal extravillous trophoblast cells are not fixed prior to treating the fetal extravillous trophoblast cells with the DNAse.

Item 20. The method of any of items 10-19, wherein the purified fetal genomic DNA is characterized by a fetal fraction in the range of 10%-100%.

Item 21. The method of any of items 10-20, wherein the purified fetal genomic DNA is characterized by a fetal fraction in the range of 25%-100%.

Item 22. A method of isolating DNA of a fetus of an ongoing pregnancy substantially as described herein.

Item 23. A method of assaying DNA of a fetus of an ongoing pregnancy with single base resolution substantially as described herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of isolating DNA of a fetus of an ongoing pregnancy, comprising:
   obtaining a maternal endocervical sample containing maternal cells and fetal extravillous trophoblast cells from a pregnant subject;
   isolating fetal extravillous trophoblast cells from the maternal endocervical sample, producing isolated fetal extravillous trophoblast cells contaminated with contaminating maternal DNA;
   lysing the isolated fetal extravillous trophoblast cells;
   isolating fetal nuclei from the lysed fetal extravillous trophoblast cells, producing isolated fetal nuclei, thereby removing at least a portion of the contaminating maternal DNA;
   lysing the isolated fetal nuclei;
   treating the isolated fetal nuclei, the isolated extravillous trophoblast cells, and/or the extravillous trophoblast cells with a DNase to remove at least a portion of the contaminating maternal DNA; and
   purifying genomic DNA from the isolated fetal nuclei, producing purified fetal genomic DNA.

2. The method of claim 1, wherein treating the isolated fetal nuclei with the DNAse is prior to lysing the isolated fetal nuclei, thereby removing at least a portion of the contaminating maternal DNA.

3. The method of claim 1, wherein treating the extravillous trophoblast cells with the DNAse is prior to isolating fetal extravillous trophoblast cells from the maternal endocervical sample, thereby removing at least a portion of the contaminating maternal DNA.

4. The method of claim 1, wherein treating the isolated extravillous trophoblast cells with the DNAse is prior to lysing isolated fetal extravillous trophoblast cells, thereby removing at least a portion of the contaminating maternal DNA.

5. The method of claim 1, wherein the fetal extravillous trophoblast cells are fixed prior to treating the fetal extravillous trophoblast cells with the DNAse and the DNAse is attached to a support, preventing entry of the DNAse into the fetal extravillous trophoblast cells.

6. The method of claim 1, wherein the fetal extravillous trophoblast cells are not fixed prior to treating the fetal extravillous trophoblast cells with the DNAse.

7. The method of claim 1, wherein the purified fetal genomic DNA is characterized by a fetal fraction in the range of 10%-100%.

8. The method of claim 1, wherein the purified fetal genomic DNA is characterized by a fetal fraction in the range of 25%-100%.

9. A method of assaying DNA of a fetus of an ongoing pregnancy, comprising:
   obtaining a maternal endocervical sample containing fetal extravillous trophoblast cells from a pregnant subject;
   isolating fetal extravillous trophoblast cells from the maternal endocervical sample;
   lysing the isolated fetal extravillous trophoblast cells;
   isolating fetal nuclei from the lysed fetal extravillous trophoblast cells;
   lysing the isolated fetal nuclei and purifying genomic DNA from the isolated fetal nuclei;
   treating the isolated fetal nuclei, the isolated extravillous trophoblast cells, and/or the extravillous trophoblast cells with a DNase to remove at least a portion of contaminating maternal DNA; and
   assaying the purified fetal genomic DNA, thereby determining a characteristic of a genomic DNA sequence of the purified fetal genomic DNA, and thereby assaying genomic DNA of a fetus of an ongoing pregnancy.

10. The method of claim 9, wherein assaying the purified fetal genomic DNA determines a characteristic of at least one individual nucleotide in a genomic DNA sequence of the purified fetal genomic DNA, thereby assaying DNA of a fetus of an ongoing pregnancy with single base resolution.

11. The method of claim 9, wherein the assaying comprises a method selected from the group consisting of: sequencing, high resolution melt analysis, methylation analysis, capillary electrophoresis, mass spectrometry, single strand conformation polymorphism, single base extension, restriction fragment length polymorphism.

12. The method of claim 9, wherein the sequencing comprises a method selected from the group consisting of: massively parallel signature sequencing, single-molecule real-time sequencing, polony sequencing, ion semiconductor, pyrosequencing, sequencing by synthesis, sequencing by ligation and chain termination sequencing.

13. The method of claim 9, wherein treating the isolated fetal nuclei with a DNAse is prior to lysing the isolated fetal nuclei, thereby removing at least a portion of the contaminating maternal DNA.

14. The method of claim 9, wherein treating the extravillous trophoblast cells with a DNAse is prior to isolating fetal extravillous trophoblast cells from the maternal endocervical sample, thereby removing at least a portion of the contaminating maternal DNA.

15. The method of claim 9, wherein treating the isolated extravillous trophoblast cells with a DNAse is prior to lysing isolated fetal extravillous trophoblast cells, thereby removing at least a portion of the contaminating maternal DNA.

16. The method of claim 9, wherein the fetal extravillous trophoblast cells are fixed prior to treating the fetal extravillous trophoblast cells with the DNAse and the DNAse is attached to a support, preventing entry of the DNAse into the fetal extravillous trophoblast cells.

17. The method of claim 9, wherein the fetal extravillous trophoblast cells are not fixed prior to treating the fetal extravillous trophoblast cells with the DNAse.

18. The method of claim 9, wherein the purified fetal genomic DNA is characterized by a fetal fraction in the range of 10%-100%.

19. The method of claim 9, wherein the purified fetal genomic DNA is characterized by a fetal fraction in the range of 25%-100%.

* * * * *